United States Patent
Kitai et al.

(10) Patent No.: US 10,561,760 B2
(45) Date of Patent: *Feb. 18, 2020

(54) SPACE MODULATION APPARATUS

(71) Applicant: Panasonic Intellectual Property Management Co., Ltd., Osaka (JP)

(72) Inventors: Takahiro Kitai, Hyogo (JP); Genichiro Matsuda, Nara (JP); Yoshio Yamada, Hyogo (JP); Gaku Miyake, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 84 days.

This patent is subject to a terminal disclaimer.

(21) Appl. No.: 15/959,105

(22) Filed: Apr. 20, 2018

(65) Prior Publication Data

US 2018/0344889 A1 Dec. 6, 2018

(30) Foreign Application Priority Data

Jun. 1, 2017 (JP) .................. 2017-109390

(51) Int. Cl.
*A61L 9/14* (2006.01)
*A61L 2/14* (2006.01)
(Continued)

(52) U.S. Cl.
CPC ............... *A61L 9/145* (2013.01); *A61L 2/14* (2013.01); *A61L 2/186* (2013.01); *A61L 2/208* (2013.01);
(Continued)

(58) Field of Classification Search
CPC . A61L 2/14; A61L 2/186; A61L 2/208; A61L 2/22; A61L 9/14; A61L 9/145;
(Continued)

(56) References Cited

U.S. PATENT DOCUMENTS 9,661,732 B2  5/2017 Imai
2013/0272929 A1* 10/2013 Pelfrey .................. A61L 2/14
                                                                  422/186.04
(Continued)

FOREIGN PATENT DOCUMENTS

JP              4041224 B       1/2008
JP         2013-119043          6/2013
(Continued)

OTHER PUBLICATIONS

Extended European Search Report dated Oct. 18, 2018 in related European Patent Application No. 18164664.7.

*Primary Examiner* — Timothy C Cleveland
(74) *Attorney, Agent, or Firm* — Wenderoth, Lind & Ponack L.L.P.

(57) ABSTRACT

A space modification apparatus includes a treatment tank configured to generate a gas phase around a rotating center of a rotating flow of a liquid by rotating the liquid, a first electrode of which at least a part is in the treatment tank so as to be in contact with the liquid in the treatment tank, a second electrode in contact with the liquid in the treatment tank, and a power source configured to apply a voltage between the first electrode and the second electrode to generate plasma in the gas phase to generate modification components, the modification components being dissolved and dispersed in the liquid, and a modification liquid being generated and retained in a storage tank. The modification liquid is sprayed or scattered from a nozzle into a treatment target space via a supply pump in the form of mist.

9 Claims, 22 Drawing Sheets

(51) Int. Cl.
*A61L 2/22* (2006.01)
*A61L 9/22* (2006.01)
*H05H 1/48* (2006.01)
*H05H 1/24* (2006.01)
*B05B 17/04* (2006.01)
*A61L 2/18* (2006.01)
*A61L 2/20* (2006.01)
*B05B 7/24* (2006.01)

(52) U.S. Cl.
CPC ........ *A61L 2/22* (2013.01); *A61L 9/14* (2013.01); *A61L 9/22* (2013.01); *B05B 7/2491* (2013.01); *B05B 7/2494* (2013.01); *B05B 17/04* (2013.01); *H05H 1/24* (2013.01); *H05H 1/48* (2013.01); *A61L 2202/11* (2013.01); *A61L 2202/122* (2013.01); *A61L 2202/15* (2013.01); *A61L 2202/25* (2013.01); *A61L 2209/134* (2013.01); *A61L 2209/213* (2013.01); *H05H 2245/121* (2013.01)

(58) Field of Classification Search
CPC .. A61L 9/22; A61L 2202/11; A61L 2202/122; A61L 2202/15; A61L 2202/25; A61L 2209/134; A61L 2209/213; B01D 53/78; B05B 7/2491; B05B 7/2494; B05B 17/04; H05H 1/24; H05H 1/48; H05H 2245/121
See application file for complete search history.

(56) References Cited

U.S. PATENT DOCUMENTS

| | | |
|---|---|---|
| 2015/0273097 A1 | 10/2015 | Murayama et al. |
| 2016/0120013 A1 | 4/2016 | Mai |
| 2016/0361454 A1 | 12/2016 | Minamio et al. |
| 2018/0230027 A1* | 8/2018 | Miyake ................. C02F 1/4608 |

FOREIGN PATENT DOCUMENTS

| | | |
|---|---|---|
| JP | 2015-192621 | 11/2015 |
| JP | 2016-083658 | 5/2016 |
| JP | 2017-000381 | 1/2017 |
| KR | 10-2016-0034470 | 3/2016 |

* cited by examiner

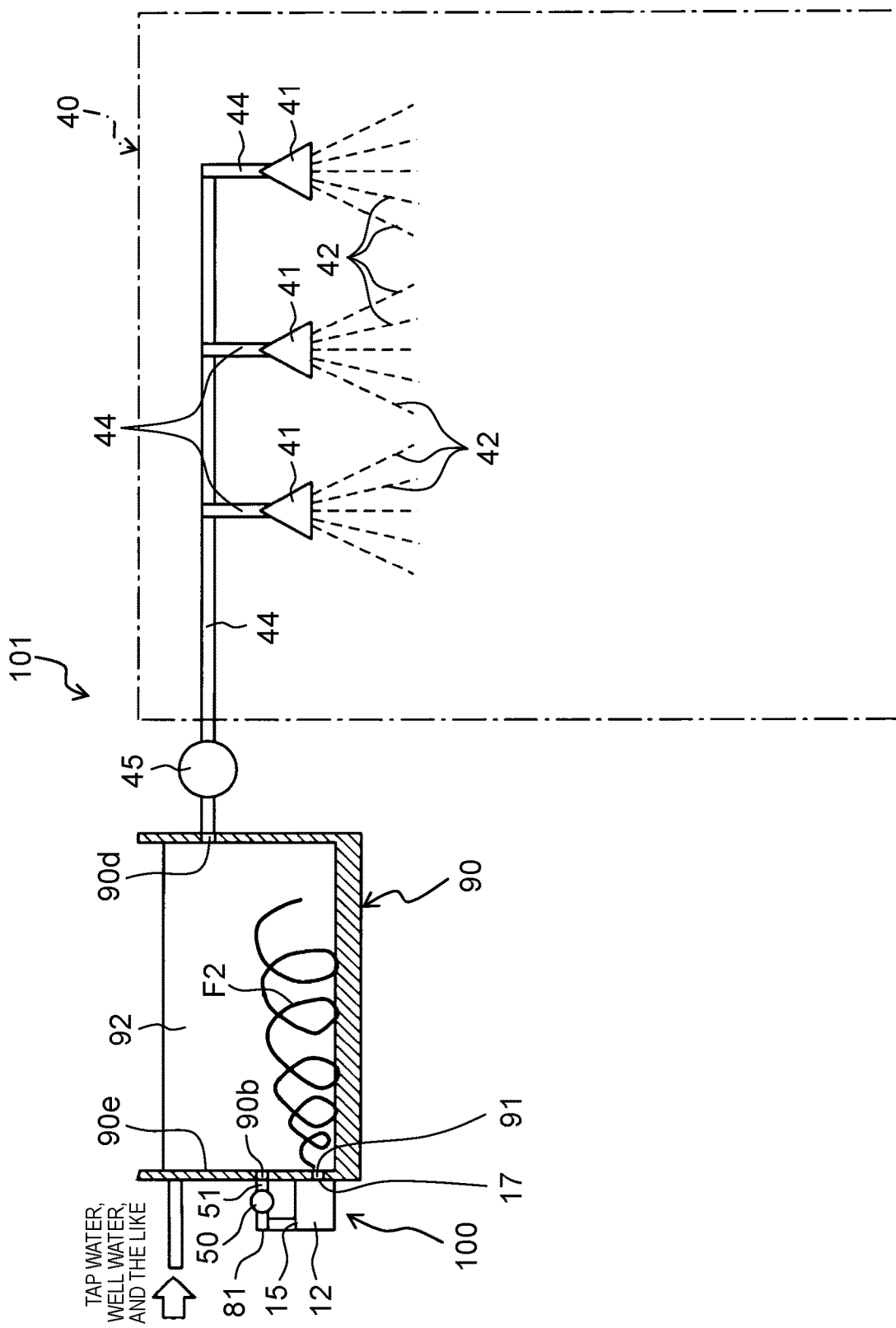

SPACE MODULATION APPARATUS

BACKGROUND

1. Technical Field

The present disclosure relates to a space modification apparatus that decomposes an odorous substance and the like by spraying modification liquid generated by a liquid treatment apparatus in mist by electrochemically treating a liquid, or captures the odorous substance and the like in the modification liquid in the form of mist to collect and thereafter decomposes the odorous substance and the like. In detail, the present disclosure relates to a space modification apparatus that reforms a liquid by generating plasma in the liquid thereby generating a modification liquid performing a bactericidal action and a deodorizing action, and decomposes the odorous substance and the like by spraying the generated modification liquid in the form of mist, or captures the odorous substance and the like in the modification liquid in the form of mist to collect and thereafter decomposes the odorous substance and the like.

2. Description of the Related Art

FIG. 15 illustrates an example of a modification liquid generating apparatus of related art. A modification liquid generating apparatus is known in which first electrode 801 and second electrode 802 are disposed in liquid 803 (for example, water) and which applies a high voltage pulse between first electrode 801 and second electrode 802 from pulse power source 804 to vaporize liquid 803 and generates plasma 805, thereby, generating a modification liquid containing components having oxidization power of, for example, hydroxyl radical (OH radical), hydrogen peroxide or the like. In particular, it is known that the OH radical has a high oxidization power and by mixing the modification liquid containing the components, a high bactericidal action is performed against, for example, bacteria. In addition, it is known that plasma 805 is covered with liquid 803 by generating plasma 805 in liquid 803 and components derived from a liquid is easily generated. For example, it is known that OH radical or hydrogen peroxide is easily generated by generating plasma 805 in water.

However, the modification liquid generating apparatus of related art has problems that not only a high application voltage is required for vaporizing liquid 803 but also generation efficiency of plasma 805 is low, and it takes a long time to modify liquid 803.

Therefore, in order to improve the generation efficiency of plasma while lowering the application voltage, a modification liquid generating apparatus is known in which gas introduced from the outside is interposed between both electrodes (refer to Japanese Patent No. 4041224). In the modification liquid generating apparatus (FIG. 16) described in Japanese Patent No. 4041224, gas 904 (for example, oxygen) is interposed between anode electrode 901 and cathode electrode 902 together with target treatment liquid 903, and thereafter, a pulse voltage is applied between anode electrode 901 and cathode electrode 902. By applying the pulse voltage, plasma is generated in gas 904 and target treatment liquid 903 is modified at a contact surface between the plasma and target treatment liquid 903. According to the modification liquid generating apparatus disclosed in Japanese Patent No. 4041224, it is possible to lower the application voltage as compared with a case where gas is not interposed, and to modify target treatment liquid 903 by efficiently generating the plasma.

It is considered to be utilized for a deodorization apparatus or a sterilization apparatus that sprays target treatment liquid 903 in the form of mist, and decomposes by coming into direct contact with an odorous substance or bacteria floating in a space, or decomposes by capturing an odorous substance or bacteria in target treatment liquid 903 in the form of mist to collect in a water tank or the like.

SUMMARY

A space modification apparatus according to an aspect of the present disclosure includes a treatment tank that generates a gas phase around a rotating center of a rotating flow of a liquid by rotating the liquid which is introduced from an introduction portion around a central axis to generate the rotating flow, and includes a discharging portion which discharges the liquid as a modification liquid after the generating the rotating flow by rotating the liquid which is introduced from the introduction portion between the introduction portion and the discharging portion, a first electrode of which at least a part is disposed in the treatment tank so as to be in contact with the liquid in the treatment tank, a second electrode which is disposed so as to be in contact with the liquid in the treatment tank, a power source which applies a voltage between the first electrode and the second electrode to generate plasma in the gas phase to generate modification components in the modification liquid, a storage tank that stores the modification liquid which is discharged from the discharging portion of the treatment tank, a pump that reintroduces stored water which is discharged into and retained in the storage tank as the modification liquid from the introduction portion of the treatment tank in the treatment tank, and allows the stored water to circulate between the treatment tank and the storage tank, a nozzle that is connected to a stored water discharging portion of the storage tank and discharges the stored water in the storage tank into a treatment target space in a form of mist, and a supply pump that supplies the stored water from the storage tank to the nozzle, in which the stored water is sprayed or scattered from the nozzle.

According to the space modification apparatus of the aspect of the present disclosure, a modification liquid having modification components is generated by vaporizing a liquid in a rotating flow and generating plasma by applying a pulse voltage to the generated gas phase. Since it is not necessary to vaporize a liquid by applying a voltage, it is possible to efficiently generate the plasma with a low electric power, to efficiently and quickly modify the liquid, and to improve an ability to decompose in direct contact with an odorous substance and bacteria without lack of components having oxidization power of the modification liquid. In addition, by spraying or scattering the modified modification liquid in the space in the form of mist, it is possible to effectively decompose an odorous substance and bacteria in the gas in the modification liquid, and to perform a space modification action.

BRIEF DESCRIPTION OF THE DRAWINGS

FIG. 6D is a side sectional view of a state where the modification liquid is sprayed from nozzles in the space modification apparatus;

DETAILED DESCRIPTIONS

Figure 1:
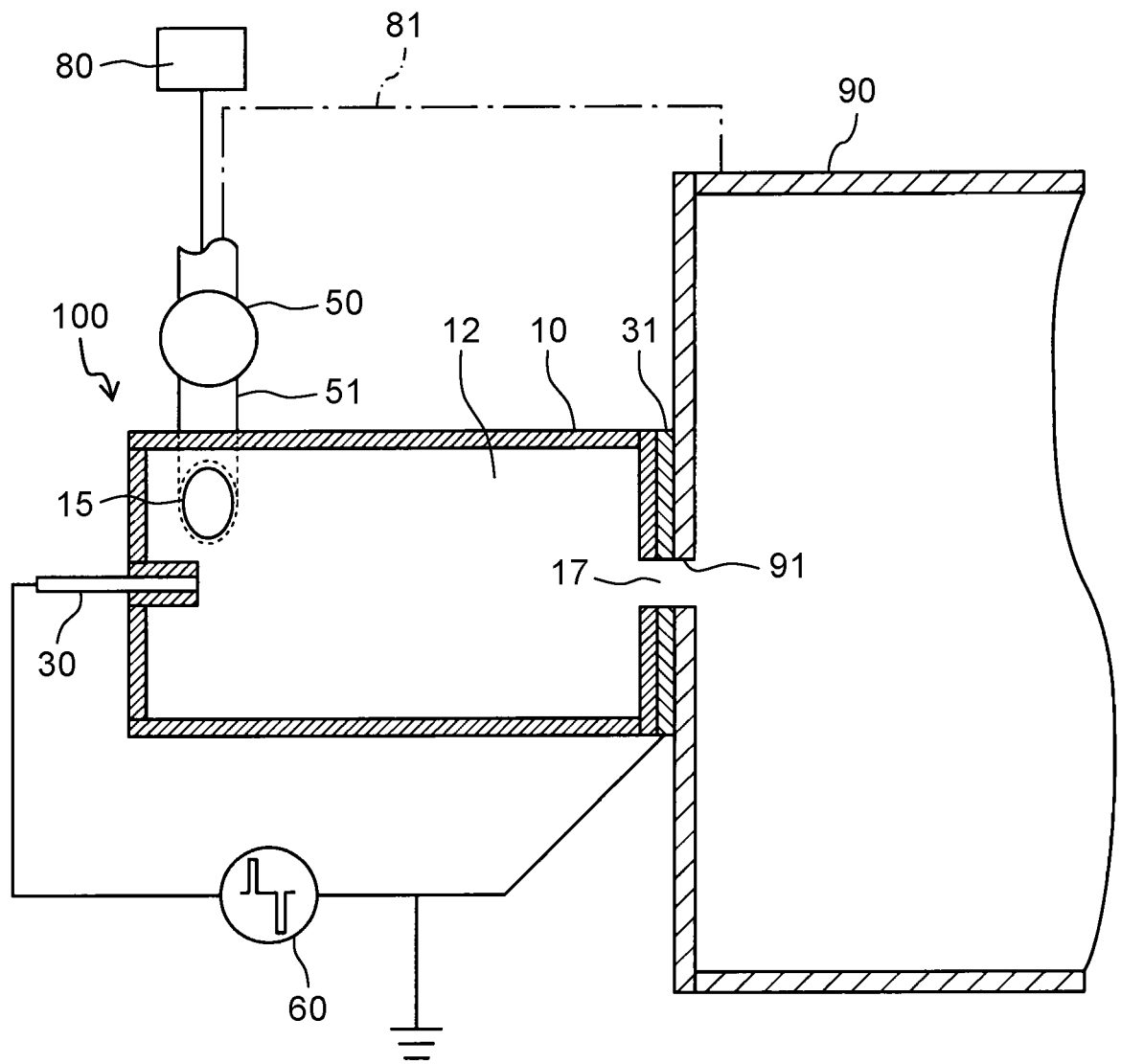
FIG. 1 is a side sectional view illustrating a configuration of a modification liquid generating apparatus of a space modification apparatus according to Embodiment 1 of the present disclosure.
Figure 1:
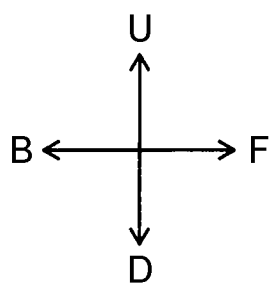

Prior to describing embodiments, problems in the related art will be briefly described.

A deodorization apparatus or a sterilization apparatus using a modification liquid generating apparatus of related art has a problem in which plasma generation efficiency is low, components having oxidization power in a modification liquid are insufficient, ability to decompose an odorous substance and bacteria is weak.

In view of the above, the present disclosure aims to provide a space modification apparatus capable of efficiently generating plasma to rapidly modify a liquid and improving the ability to decompose the odorous substance and the bacteria.

Embodiment 1

Hereinafter, space modification apparatus 101 including modification liquid generating apparatus 100 according to an embodiment of the present disclosure will be described in detail with reference to the drawings. In the drawings, the same symbols or reference numerals are attached to the same or corresponding portions, and description thereof will not be repeated. For the sake of easy description, a configuration is simplified or schematically illustrated, and some configuration members are omitted in the drawings referred to below. In addition, a dimensional ratio between the configuration members illustrated in the respective drawings does not necessarily indicate an actual dimensional ratio.

Entire Configuration

Figure 6A:
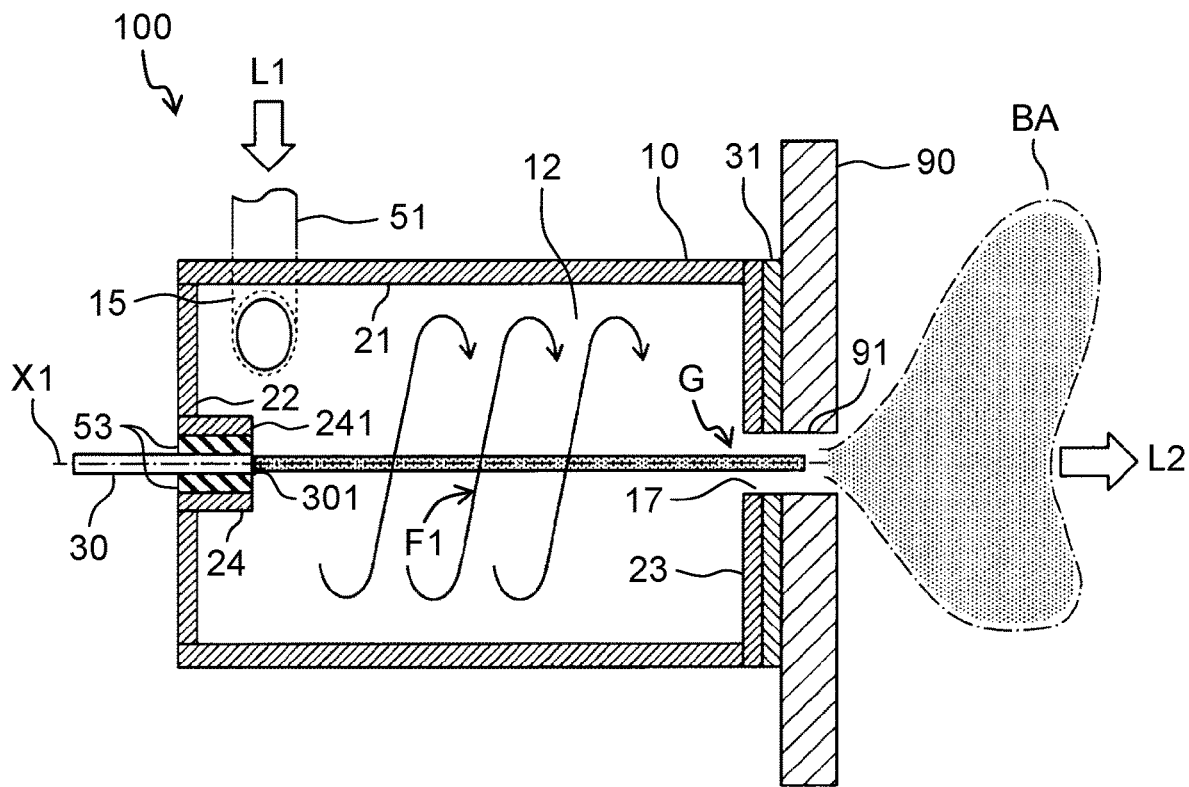
FIG. 6A is a side sectional view illustrating a state in which the rotating flow is generated in the treatment tank and a voltage is applied.

Space modification apparatus 101 includes at least modification liquid generating apparatus 100, nozzle 41, and supply pump 45 (see FIG. 6D). Modification liquid generating apparatus 100 functions as an apparatus for generating modification liquid L2 (see FIG. 6A) to be used in a deodorization treatment or sterilization treatment.

First, the entire configuration of modification liquid generating apparatus 100 according to Embodiment 1 will be described. FIG. 1 is a side sectional view illustrated a configuration of modification liquid generating apparatus 100 according to Embodiment 1 of the present disclosure. In the following drawings, arrow F indicates a forward direction of modification liquid generating apparatus 100, and arrow B indicates a backward direction. Arrow U indicates an upward direction and arrow D indicates a downward direction. Arrow R indicates a right direction as viewed from the backward direction, and arrow L indicates a left direction as viewed from the backward direction.

Modification liquid generating apparatus 100 generates modification components according to discharge in liquid and disperses the generated modification components in the liquid to generate modification liquid L2. In Embodiment 1, a case where circulation water L1 (see FIG. 6A) is modified as an example of liquid to generate modification liquid L2 containing modification components such as OH radical or hydrogen peroxide will be described. Here, circulation water L1 indicates stored water 92 retained and stored in storage tank 90, which will be described below with reference to FIG. 6D, which is supplied to treatment tank 12 via circulation pipe 81 and pipe 51 by a pump that is an example of liquid supplier 50. Tap water, well water or the like can be supplied from supply port 90e for circulation water L1.

Modification liquid generating apparatus 100 includes at least treatment tank 12, first electrode 30, second electrode 31, and power source 60. More specifically, modification liquid generating apparatus 100 includes apparatus main body 10, liquid supplier 50, storage tank 90, and power source 60. Apparatus main body 10 includes treatment tank 12, introduction portion 15, discharging portion 17, first electrode 30, and second electrode 31.

Treatment tank 12 is a portion that generates modification liquid L2 by generating modification components using plasma from circulation water L1 introduced therein. A material of treatment tank 12 may be an insulator or a conductor. In a case where the material is a conductor, it is necessary to interpose an insulator between treatment tank 12 and first electrode 30, and between treatment tank 12 and second electrode 31. When the modification components are discharged to storage tank 90, the modification components are dispersed in circulation water L1 and modification liquid L2 is generated.

Treatment tank 12 includes a cylindrical treatment chamber of which front sectional shape is circular. Introduction portion 15 is disposed at one end of treatment tank 12 and introduces circulation water L1 into treatment tank 12 from a tangential direction of a circular cross section shape orthogonal to central axis X1 of treatment tank 12. Introduction portion 15 communicates with liquid supplier 50 via pipe 51. Discharging portion 17 is disposed at the other end of treatment tank 12 and discharges circulation water L1 introduced into treatment tank 12 and the modification components generated in treatment tank 12 from treatment tank 12 to storage tank 90. In Embodiment 1, discharging portion 17 is connected to modification liquid supplier 91 of storage tank 90.

First electrode 30 is disposed inside one end of treatment tank 12. First electrode 30 is disposed in treatment tank 12 so as to protrude from the center of an inner wall of one end of treatment tank 12 in a longitudinal direction.

Second electrode 31 is disposed outside a wall at the other end of treatment tank 12 and is disposed around discharging portion 17.

First electrode 30 is connected to power source 60, and second electrode 31 is grounded. A high pulse voltage is applied to first electrode 30 and second electrode 31 by power source 60. For example, tungsten is used as a material of first electrode 30.

For example, liquid supplier 50 is a pump supplying circulation water L1 into treatment tank 12. Liquid supplier 50 is connected to pipe 51. One end of pipe 51 is connected to introduction portion 15 as an inner opening disposed around an inner wall of one end of treatment tank 12 and the other end of pipe 51 is connected to a liquid supply source (for example, water tank 80) not illustrated or in a shape capable of circulating the stored water containing a modification liquid in storage tank 90.

Power source 60 applies a high pulse voltage between first electrode 30 and second electrode 31. Power source 60 can alternately apply a positive pulse voltage and a negative pulse voltage, a so-called bipolar pulse voltage.

Storage tank 90 is a tank for shearing the modification components discharged from modification liquid generating apparatus 100, generating microbubbles or nanobubbles containing the modification components, and diffusing the microbubbles or nanobubbles into water. Specifically, storage tank 90 has a cross section area larger than a cross section area of the opening of discharging portion 17 of treatment tank 12 therein, shears the modification components discharged from discharging portion 17 into storage tank 90, in storage tank 90, generates the microbubbles containing the modification component or the microbubbles and nanobubbles in storage tank 90, and diffuses the microbubbles and nanobubbles into water. Therefore, storage tank 90 functions as a microbubble generation tank. By securing an inner diameter or one side which is twice an inner diameter of an opening of discharging portion 17 of treatment tank 12 as storage tank 90, modification liquid L2 containing microbubbles or nanobubbles and reliably performing sterilization can be generated in storage tank 90.

As illustrated in FIG. 6D, storage tank 90 includes modification liquid supplier 91 disposed at a lower portion or a middle portion thereof and connected to discharging portion 17 of treatment tank 12, stored water discharging portion 90b disposed at an upper portion above modification liquid supplier 91, for example, disposed at the center, and stored water discharging portion 90d disposed at the upper portion. As an example, modification liquid supplier 91 and stored water discharging portion 90b are disposed on treatment tank 12 side, and stored water discharging portion 90d is disposed on a side separated from modification liquid supplier 91 and stored water discharging portion 90b, for example, on a side oppose thereto. Modification components are generated by generating plasma P (see FIG. 6B, details will be described below) in gas phase G in treatment tank 12. The generated modification components are dissolved in the liquid and dispersed in the liquid to generate modification liquid L2, and generated modification liquid L2 is discharged from discharging portion 17 of treatment tank 12 into modification liquid supplier 91 of the storage tank 90 and is stored in storage tank 90 after becoming a water flow with a rotating flow (refer to whirlpool F2 in FIG. 6D).

In FIG. 6D, pipe 51 is connected to stored water discharging portion 90b of storage tank 90 and configures circulation pipe 81. Stored water 92 in storage tank 90 is supplied from introduction portion 15 into treatment tank 12 via circulation pipe 81 and liquid supplier 50 as circulation water L1, and is configured to circulate between treatment tank 12 and storage tank 90 as modification liquid L2 discharged from treatment tank 12 via discharging portion 17 is introduced into storage tank 90 from modification liquid supplier 91. A liquid level of stored water 92 including modification liquid L2 in storage tank 90 is maintained above stored water discharging portion 90b and stored water discharging portion 90d. Following Embodiment 2 and Embodiment 3 have the same configuration.

In addition to modification liquid generating apparatus 100, space modification apparatus 101 further includes nozzles 41 and supply pump 45.

Supply pump 45 is provided in the middle of modification liquid supply pipe 44, one end of modification liquid supply pipe 44 is connected to stored water discharging portion 90d, and the other end is connected to one or a plurality of nozzles 41.

Nozzles 41 are arranged, for example, above treatment target space 40, and discharge modification liquid L2 supplied from stored water discharging portion 90d of storage tank 90 via modification liquid supply pipe 44 from above treatment target space 40 in the form of mist. Spraying, scattering or the like can be exemplified as a discharging method. Treatment target space 40 may be a closed space such as an indoor space or an open space such as an outdoor space. Modification liquid L2 can be decomposed by being discharged in the form of mist to come into direct contact with an odorous substance or bacteria floating in the gas.

Apparatus Main Body

Next, apparatus main body 10 will be described in detail. FIG. 2 is a side sectional view of apparatus main body 10.

Treatment tank 12 includes first inner wall 21, second inner wall 22, and third inner wall 23. First inner wall 21 is a cylindrical wall portion. Second inner wall 22 is provided at a left end portion of first inner wall 21 in FIG. 2. Third inner wall 23 is provided at a right end portion of first inner wall 21 in FIG. 2. Second inner wall 22 and third inner wall 23 are substantially circular in a side view. First inner wall 21, second inner wall 22, and third inner wall 23 configure substantially columnar accommodation space 83 inside treatment tank 12. A central axis of first inner wall 21, that is, an imaginary central axis of substantially columnar accommodation space 83 configured inside treatment tank 12 is referred to as central axis X1.

Cylindrical electrode support tube 24 protruding into accommodation space 83 is provided in the center of second inner wall 22. Electrode support tube 24 is cylindrical and extends toward the right. Electrode support tube 24 is disposed such that a central axis thereof coincides with central axis X1. First electrode 30 is supported inside electrode support tube 24 via an insulator 53. First electrode 30 has a rod shape, and insulator 53 is disposed around first electrode 30. First electrode 30 is disposed such that a longitudinal axis coincides with central axis X1. An inner end surface of right end portion 301 of first electrode 30, inner end surface of insulator 53, and an inner end surface 241 of electrode support tube 24 are configured to be arranged in substantially the same plane.

Figure 2:
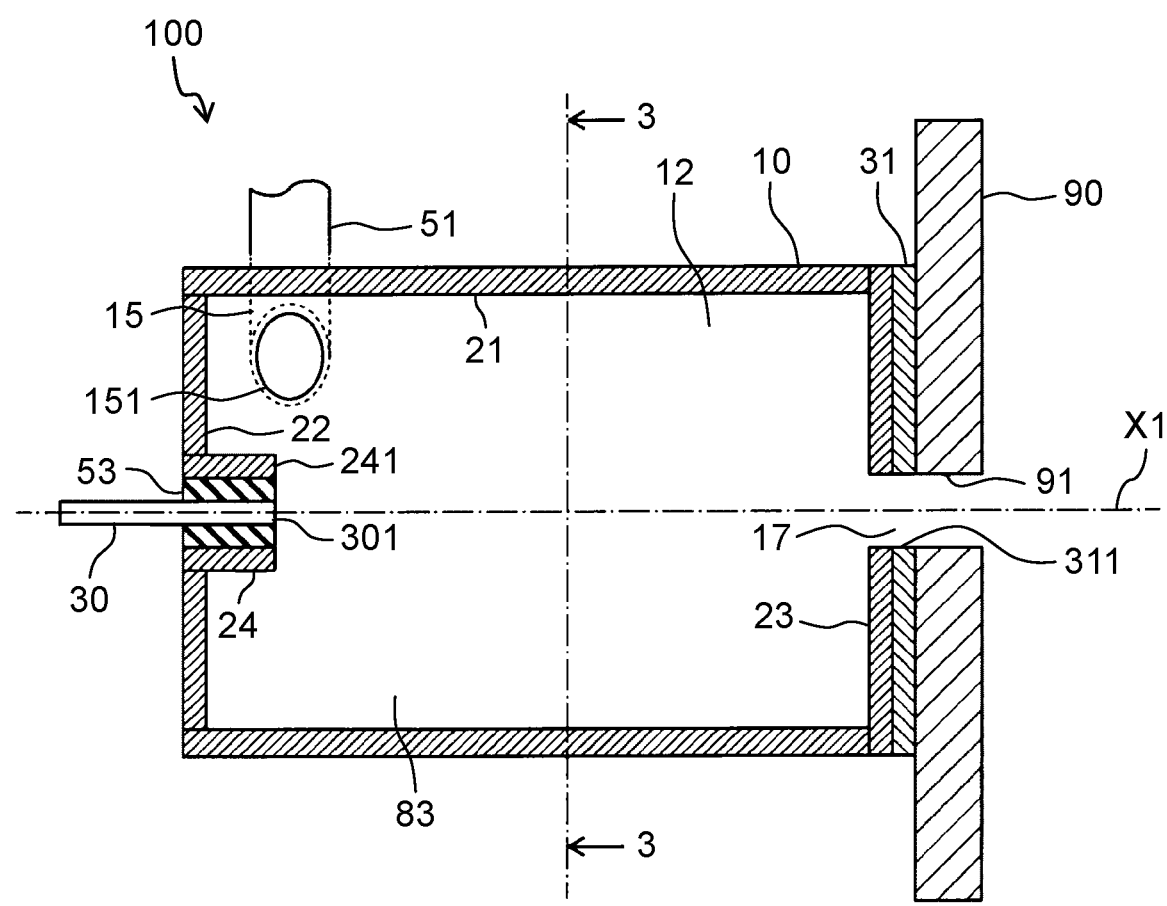
FIG. 2 is a side sectional view of an apparatus main body.
Figure 2:
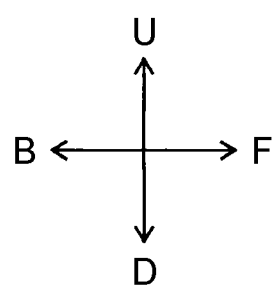
Figure 3:
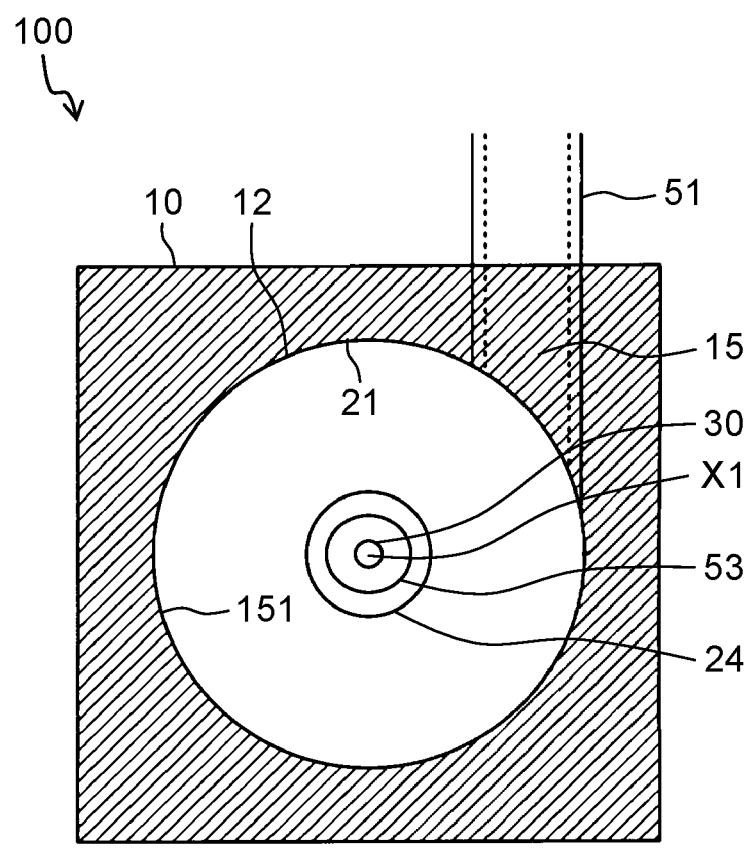
FIG. 3 is a cross-sectional view taken along line 3-3 of FIG. 2.
Figure 3:
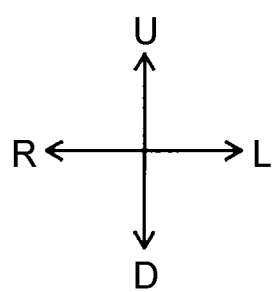

Introduction portion 15 penetrates apparatus main body 10, and one opening end 151 is formed in first inner wall 21. In the side view, introduction portion 15 is disposed at a position adjacent to second inner wall 22. In addition, FIG. 3 is a cross-sectional view taken along line 3-3 of FIG. 2. Introduction portion 15 is disposed on a wall surface of first inner wall 21.

Discharging portion 17 penetrates a central portion of third inner wall 23. Discharging portion 17 is formed such that a central axis thereof coincides with central axis X1.

Second electrode 31 is a plate-shaped metal member, and opening 311 is formed in the center. Opening 311 has a circular shape and a central axis thereof coincides with central axis X1.

Operation

Figure 4:
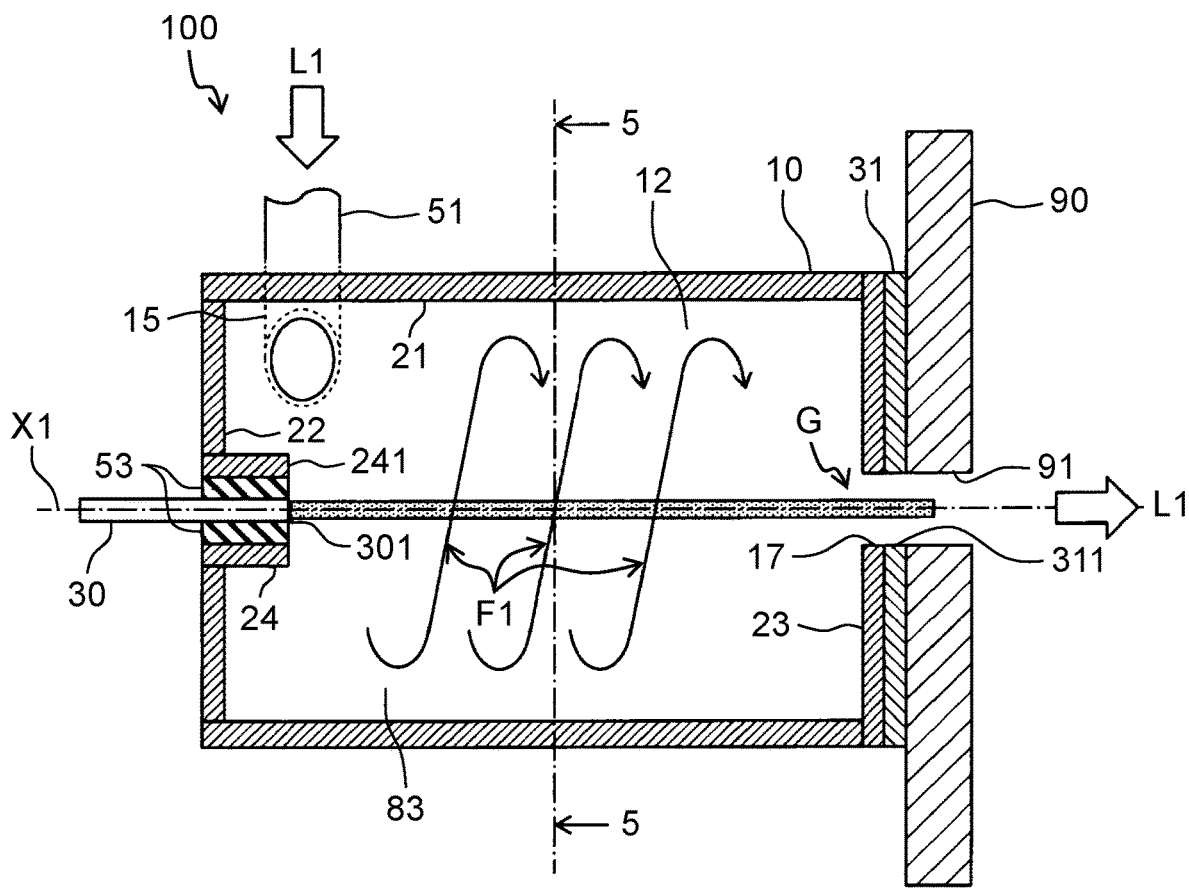
FIG. 4 is a side sectional view illustrating a state in which a rotating flow is generated in a treatment tank and no voltage is applied.
Figure 4:
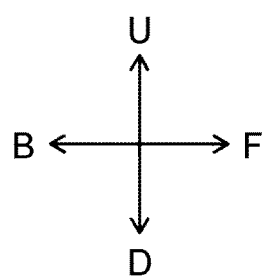

Next, an operation of modification liquid generating apparatus 100 will be described. Hereinafter, for the sake of convenient description, a state in which a gas phase is generated in treatment tank 12 (FIGS. 4 and 5) and a state in which a pulse voltage is applied to generated gas phase G to generate plasma P (FIGS. 6A and 6B) will be described separately. FIG. 4 is a side sectional view illustrating a state in which rotating flow F1 is generated in treatment tank 12 and no pulse voltage is applied.

First, as illustrated in FIG. 4, stored water 92 in storage tank 90 is sucked in by a pump (liquid supplier 50, see FIG. 1) and is introduced from introduction portion 15 into treatment tank 12 as circulation water L1 by a predetermined pressure. Then, circulation water L1 moves along first inner wall 21 from introduction portion 15 toward the right side in FIG. 4 while generating rotating flow F1. Rotating flow F1 moved to the right of FIG. 4 while rotation moves toward discharging portion 17.

The pressure around central axis X1 is decreased to a saturated water vapor pressure or less by rotating flow F1, and gas phase G is generated around central axis X1 by water vapor vaporized from a part of circulation water L1. Gas phase G is generated around the rotating center, more specifically, from right end portion 301 of first electrode 30 to the vicinity of opening 311 of second electrode 31 along central axis X1. In addition, gas phase G is rotating in the same direction as rotating flow F1 by rotating flow F1 in contact therewith. Rotating gas phase G is sheared to be microbubbles or nanobubbles due to resistance of water in storage tank 90 around discharging portion 17 and is diffused from discharging portion 17 to storage tank 90 via the modification liquid supplier 91 of storage tank 90 connected to discharging portion 17.

Figure 5:
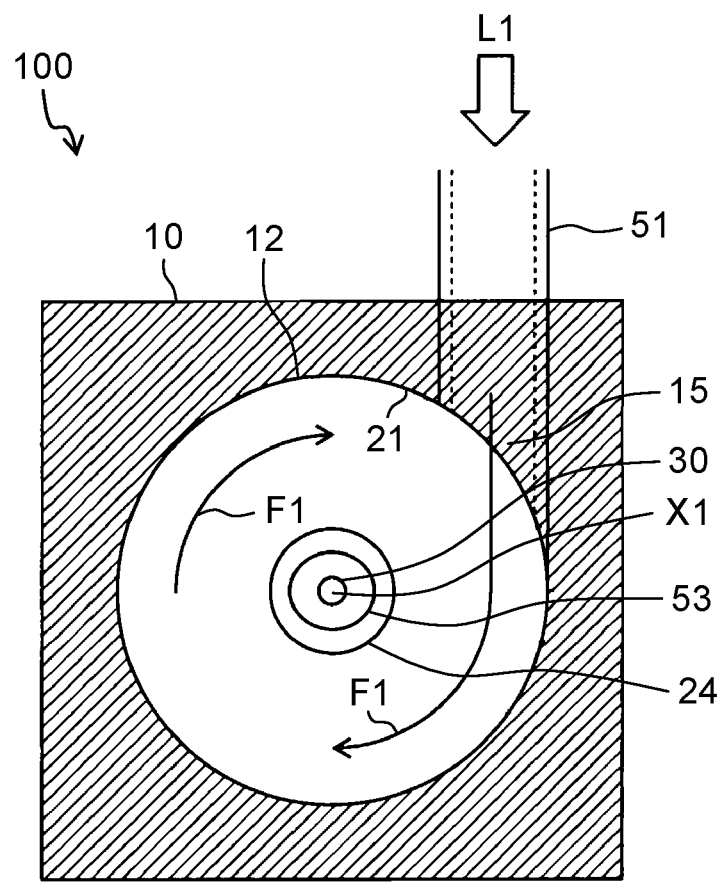
FIG. 5 is a cross-sectional view taken along line 5-5 of FIG. 4.
Figure 5:
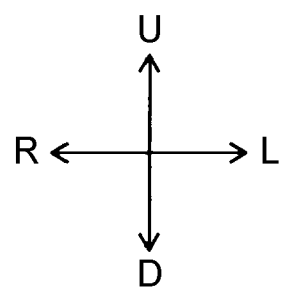

FIG. 5 is a cross-sectional view taken along line 5-5 of FIG. 4. As described with reference to FIG. 4, if circulation water L1 is introduced from introduction portion 15 to treatment tank 12 by a predetermined pressure, circulation water L1 generates clockwise rotating flow F1 in FIG. 5 along first inner wall 21. As circulation water L1 rotates in treatment tank 12, pressure around the center of rotating flow F1, that is, pressure around central axis X1 decreases to saturated water vapor pressure or less, and water vapor vaporized from a part of circulation water L1 is generated around central axis X1, and thereby, gas phase G is generated.

Figure 6B:
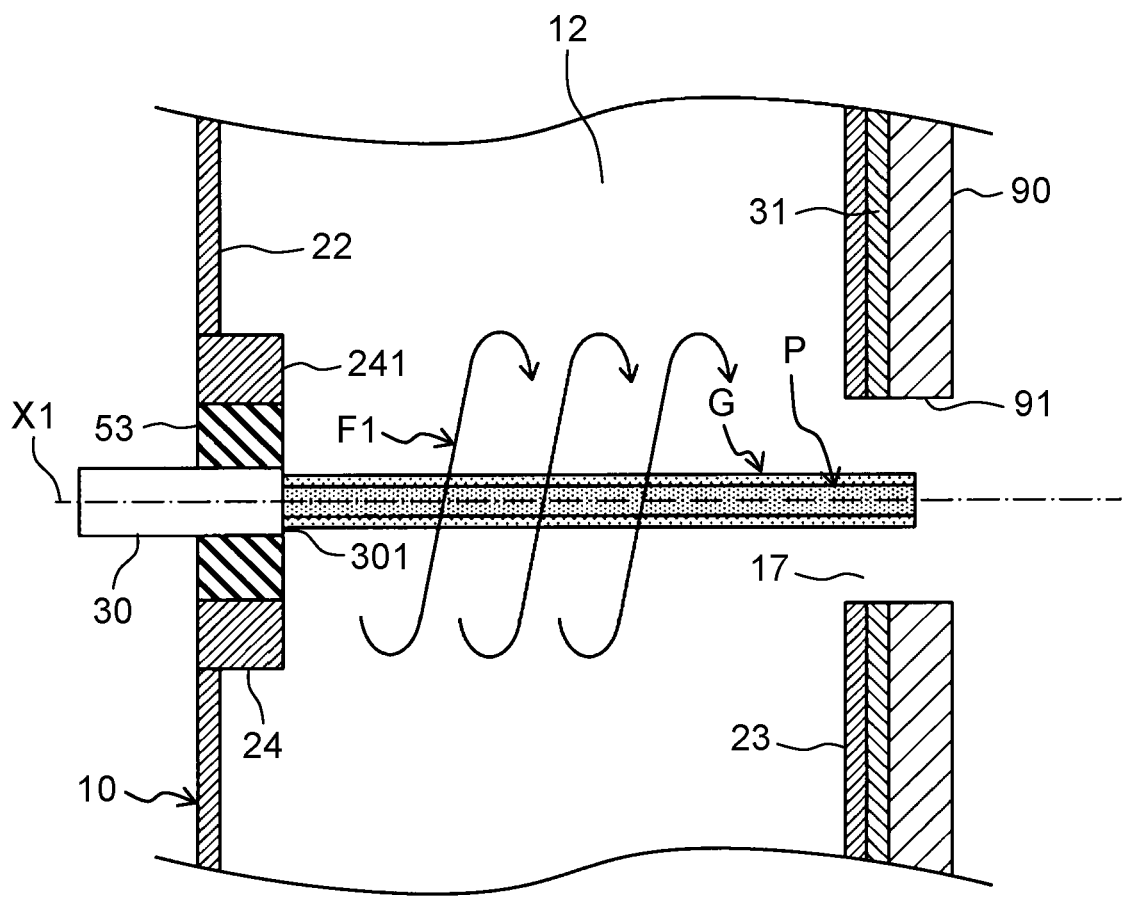
FIG. 6B is a partially enlarged view of a state in which plasma is generated in a gas phase of FIG. 6A.
Figure 6B:
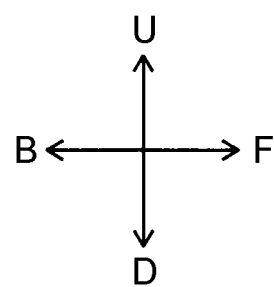
Figure 6C:
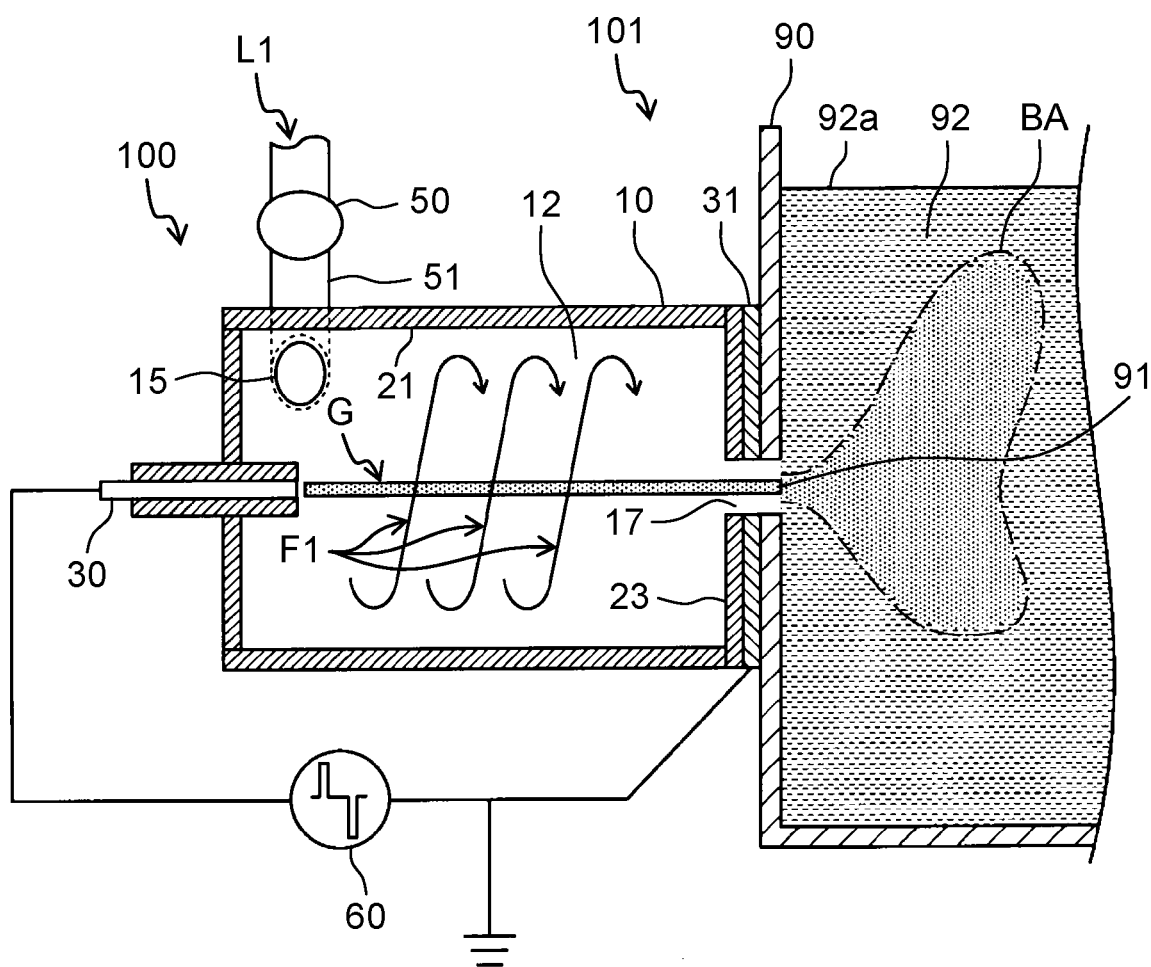
FIG. 6C is a side sectional view illustrating a state where a modification liquid is supplied to a storage tank of the space modification apparatus.
Figure 6E:
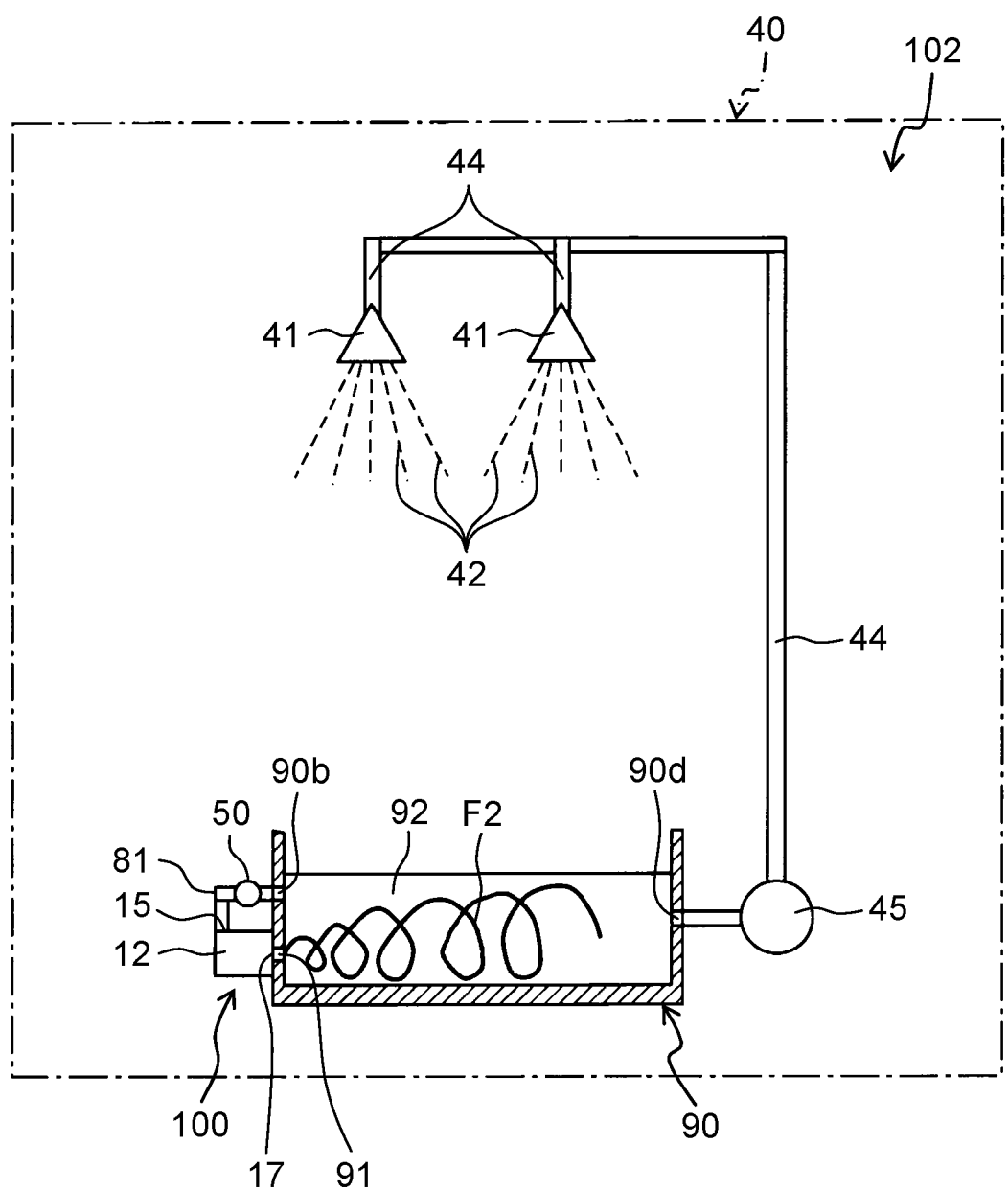
FIG. 6E is a side sectional view illustrating a configuration of a space modification apparatus according to Embodiment 2 of the present disclosure.
Figure 6F:
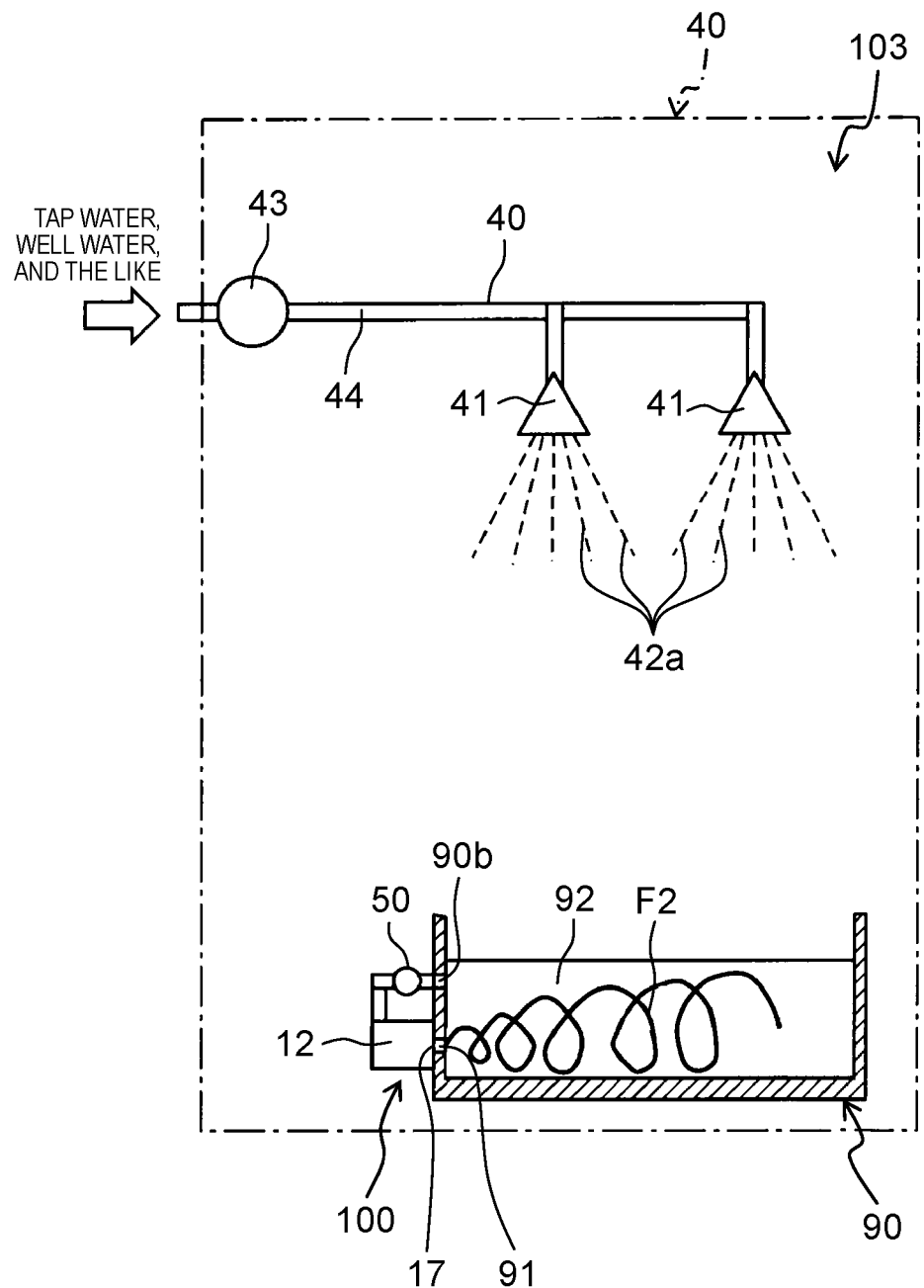
FIG. 6F is a side sectional view illustrating a configuration of a space modification apparatus according to Embodiment 3 of the present disclosure.

FIGS. 6A and 6B are side sectional views illustrating a state in which rotating flow F1 is generated in treatment tank 12 and a pulse voltage is applied. As illustrated in FIG. 6A, in a state where gas phase G vaporized from circulation water L1 is generated from the vicinity of first electrode 30 to the vicinity of second electrode 31, a high pulse voltage is applied between first electrode 30 and second electrode 31 by power source 60. FIG. 6B is an enlarged view illustrating a state in which plasma P is generated in gas phase G. If a high pulse voltage is applied between first electrode 30 and second electrode 31, plasma P is generated in gas phase G, and radical (OH radical or the like) derived from water, compound (hydrogen peroxide or the like) or ions are generated as modification components. Gas phase G containing the modification components rotates in the same direction as rotating flow F1 by rotating flow F1 in the periphery. As gas phase G containing the modification components rotates, a part of the modification components dissolves toward rotating flow F1, and thereby, the modification components are dispersed in circulation water L1. In addition, gas phase G containing the modification components around discharging portion 17 is sheared due to resistance of modification liquid L2 in storage tank 90 and generates air bubbles BA containing modification components. At this time, modification liquid L2 discharged into storage tank 90 from discharging portion 17 of treatment tank 12 via modification liquid supplier 91 of storage tank 90 is discharged from treatment tank 12 into storage tank 90 due to influence of rotating flow F1 in treatment tank 12, in a state where a water flow of modification liquid L2 accompanying the rotating flow and the above-described air bubbles BA are combined. Thereby, an odorous substance and bacteria decomposing components are added to stored water 92 in storage tank 90. In addition, by keeping modification liquid L2 in storage tank 90, air is prevented from being mixed into gas phase G which is a negative pressure. In this manner, modification liquid L2 is stored in storage tank 90 as stored water 92 in a state where modification components generated by plasma P are air bubbles or are dissolved and dispersed in modification liquid L2.

Thereafter, supply pump 45 is driven to suck up stored water 92 become modification liquid L2 in storage tank 90 and supplies the stored water to modification liquid supply pipe 44. Modification liquid L2 is sprayed or scattered from above treatment target space 40 in the form of mist from nozzle 41 at a front end of modification liquid supply pipe 44. As a result, mist 42 of modification liquid L2 to which decomposing components for decomposing an odorous substance are added is supplied to treatment target space 40, and the odorous substance or bacteria in the gas such as air is decomposed by modification liquid L2.

While not illustrated in detail, a configuration may be provided in which an odorous substance is forcibly sucked into treatment target space 40 from a separate space by a fan and the sucked odorous substance is decomposed in treatment target space 40. Such a configuration is also applicable to Embodiment 2 and Embodiment 3 which will be described below.

According to Embodiment 1 described above, circulation water L1 is vaporized in rotating flow F1, a pulse voltage is applied to the generated gas phase G to generate plasma P, and thereby, modification liquid L2 containing modification components are generated from liquid. Therefore, gas phase G has a more negative pressure than gas vaporized by Joule heat or a gas phase formed by gas introduced from the outside, and plasma P can be generated by a small voltage (that is, low electric power), and thereby, modification treatment of circulation water L1 can be efficiently performed, components having oxidization power in the modification liquid is not insufficient, and ability to come into direct contact with an odorous substance and bacteria to decompose can be improved. Furthermore, since water is not vaporized by Joule heat, the energy to be input is reduced. In addition, since gas is not introduced from the outside, a gas supply apparatus is not required, and the modification liquid generating apparatus can be easily downsized. That is, a configuration of space modification apparatus 101 having modification liquid generating apparatus 100 is compact as a whole, active species can be efficiently generated, the odorous substance and bacteria in the gas can be effectively decomposed in modification liquid L2 by spraying or scattering in the form of mist, and a space modification action can be performed.

In addition, it is difficult to retain gas phase G formed by the gas vaporized by Joule heat or the gas introduced from the outside at a certain shape or a fixed position due to buoyancy. However, in gas phase G according to Embodiment 1, force is applied in a direction of being gathered on central axis X1 by surrounding rotating flow F1, and thus, constant gas phase G can be generated around right end portion 301 of first electrode 30. Therefore, the amount of gas generated between first electrode 30 and second electrode 31 changes little with time, and electric power required for plasma P is hard to change, and thereby, plasma P can be stably generated, and modification treatment of circulation water L1 can be performed efficiently and quickly.

In addition, a volume of plasma P is equal to or less than a volume of a gas phase around a cathode electrode, but a shape of gas phase G formed by the gas vaporized by Joule heat or the gas introduced from the outside is a bubble shape, thereby, being split if the volume is above a certain level, and thus, it is difficult to generate plasma P having a certain volume or more. However, in gas phase G according to Embodiment 1, if a rotation speed of rotating flow F1 can be secured, the volume is easily enlarged in a direction of central axis X1, and thereby, the volume of plasma P is easily increased. Therefore, it is possible to easily increase the amount of production of the modification components, and to quickly modify liquid.

In addition, since the volume expands when the liquid is vaporized, cavitation is known that generates a shock wave and destroys surrounding objects. In Embodiment 1, destruction made by cavitation is most intensified in discharging portion 17 that has the smallest inner diameter of treatment tank 12 and the fastest rotation speed of rotating flow F1. Therefore, since right end portion 301 of first electrode 30 is separated from a portion where the destruction of the cavitation is the strongest in gas phase G, influence on first electrode 30 due to the cavitation is small and plasma P can be stably generated.

In addition, in order to perform treatment of circulation water L1 without introducing air from the outside, it is possible to suppress generation of harmful nitrous acid generated by the plasma utilizing the gas phase introducing gas containing nitrogen components such as air. Furthermore, it is possible to generate modification liquid L2 containing air bubbles BA containing OH radical, hydrogen peroxide or the like.

Embodiment 2

As illustrated in FIG. 6E, storage tank 90 may be disposed below one nozzle or a plurality of nozzles 41 and an upper portion of storage tank 90 may be opened as space modification apparatus 102 according to Embodiment 2.

By adopting such a configuration, an odorous substance or bacteria in treatment target space 40 is captured by mist 42 ejected from nozzle 41. In this manner, mist 42 capturing the odorous substance or bacteria falls into stored water 92 from an upper opening of storage tank 90. Among the odorous substance or bacteria, the odorous substance or bacteria which cannot be decomposed and remains while mist 42 falls is effectively decomposed in contact with modification liquid L2 by water flow F2 of air bubbles BA and modification liquid L2 in stored water 92.

Stored water 92 in FIG. 6E also contains a modification liquid having a reduced deodorization effect by decomposing an odorous substance or bacteria captured in storage tank 90, in modification liquid L2 contained in mist 42 dropped from nozzle 41 of space modification apparatus 102 into storage tank 90 and in modification liquid L2 of mist 42. Modification liquid L2 and the like contained in mist 42 falling into storage tank 90 are also sucked as stored water 92 by liquid supplier 50 and introduced from introduction portion 15 to treatment tank 12 as circulation water L1.

According to Embodiment 2, while mist 42 is discharged from nozzle 41 and reaches storage tank 90, the odorous substance remaining without being decomposed by modification liquid L2 of mist 42 can also be decomposed by modification liquid L2 in stored water 92 of storage tank 90, and a decomposition and a sterilization action of the odorous substance and bacteria can be performed more effectively. In addition, since mist 42 can be collected and reused in storage tank 90, circulation water L1 and modification liquid L2 can be used more efficiently. Furthermore, the odorous substance or bacteria can be captured by mist 42 and decomposition can be started at the same time. Alternatively, when mist 42 is sprayed or scattered, air bubbles BA containing decomposition components are added to mist 42, and thereby, decomposition is expedited and at the same time the odorous substance falling into storage tank 90 can be effectively decomposed by water flow F2 accompanying the rotating flow discharged from treatment tank 12.

According to the configuration, addition of an odorous substance and bacteria decomposing ability to target treatment water, or stirring of the target treatment water can be provided by a unit of one configuration, and used can be used for an efficient space modification apparatus.

Embodiment 3

In space modification apparatus 103 of FIG. 6F, in the same manner as in FIG. 6E, while storage tank 90 is disposed below one nozzle or a plurality of nozzles 41 and an upper surface of storage tank 90 is in an open state, storage tank 90 is not connected to one end of modification liquid supply pipe 41 to which nozzle 44 is connected, and tap water, well water, or the like is supplied by external pump 43.

In this configuration, an odorous substance or bacteria in treatment target space 40 is captured to mist 42*a* such as tap water ejected from nozzle 41. In this way, mist 42*a* capturing the odorous substance or the bacteria falls into stored water 92 of storage tank 90 and efficiently comes into contact with modification liquid L2 by water flow F2 of air bubbles BA and modification liquid L2 in stored water 92, and the odorous substance or the bacteria is decomposed.

According to Embodiment 3, configurations of nozzle 41 for blowing out mist 42a, external pump 43, and the like can be made by using a known configuration of related art, and the entire apparatus can be inexpensively configured.

Modification Example

The configuration of modification liquid generating apparatus 100 described in Embodiment 1 to Embodiment 3 is an example, and various modifications can be made. For example, an internal structure of treatment tank 12, a position of first electrode 30 or second electrode 31, and the like are not limited to the structures of Embodiment 1 to Embodiment 3.

Figure 7:
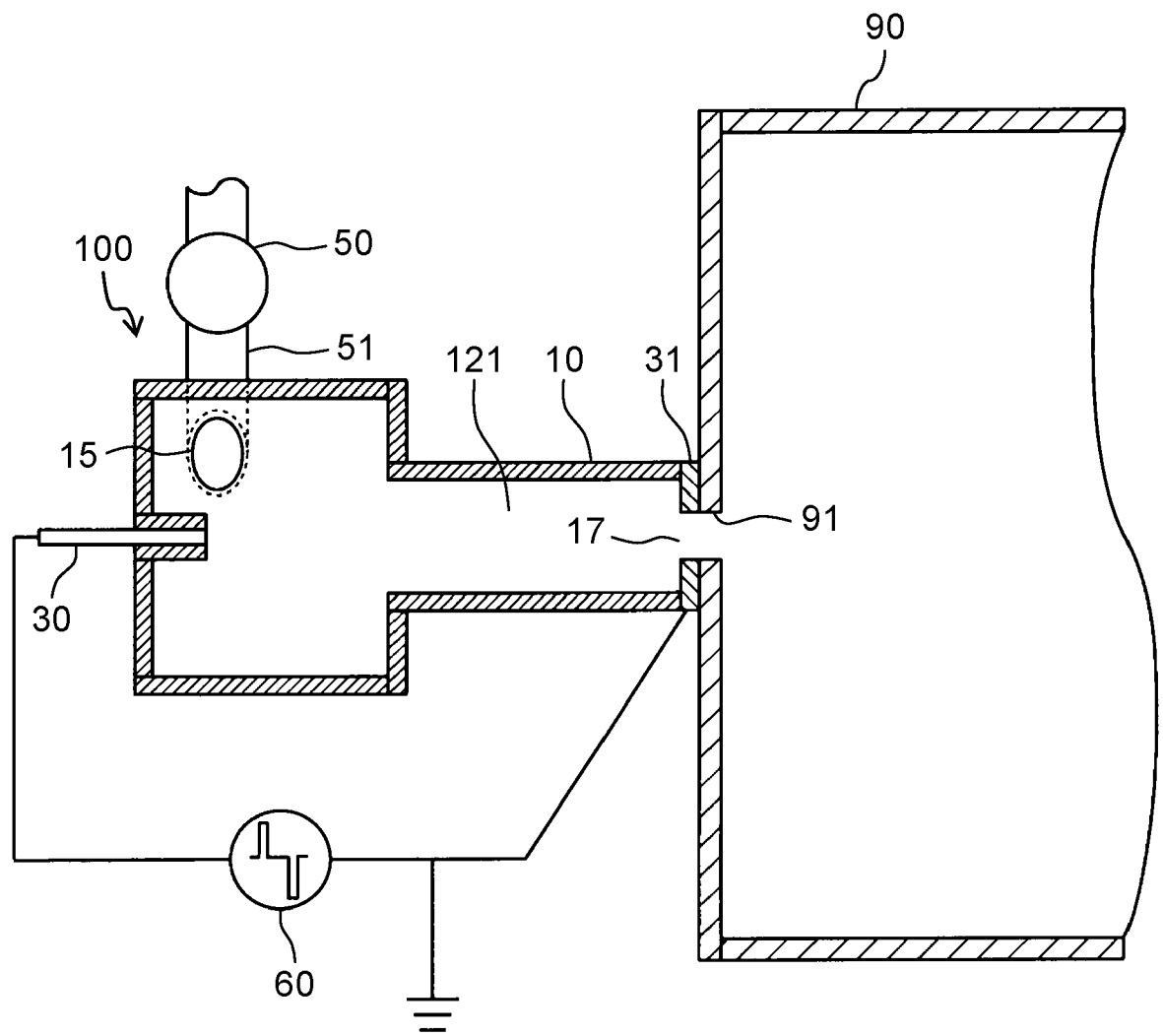
FIG. 7 is a side sectional view illustrating a modification example of the apparatus main body.
Figure 7:
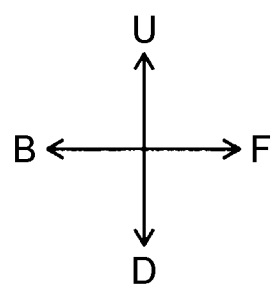
Figure 8:
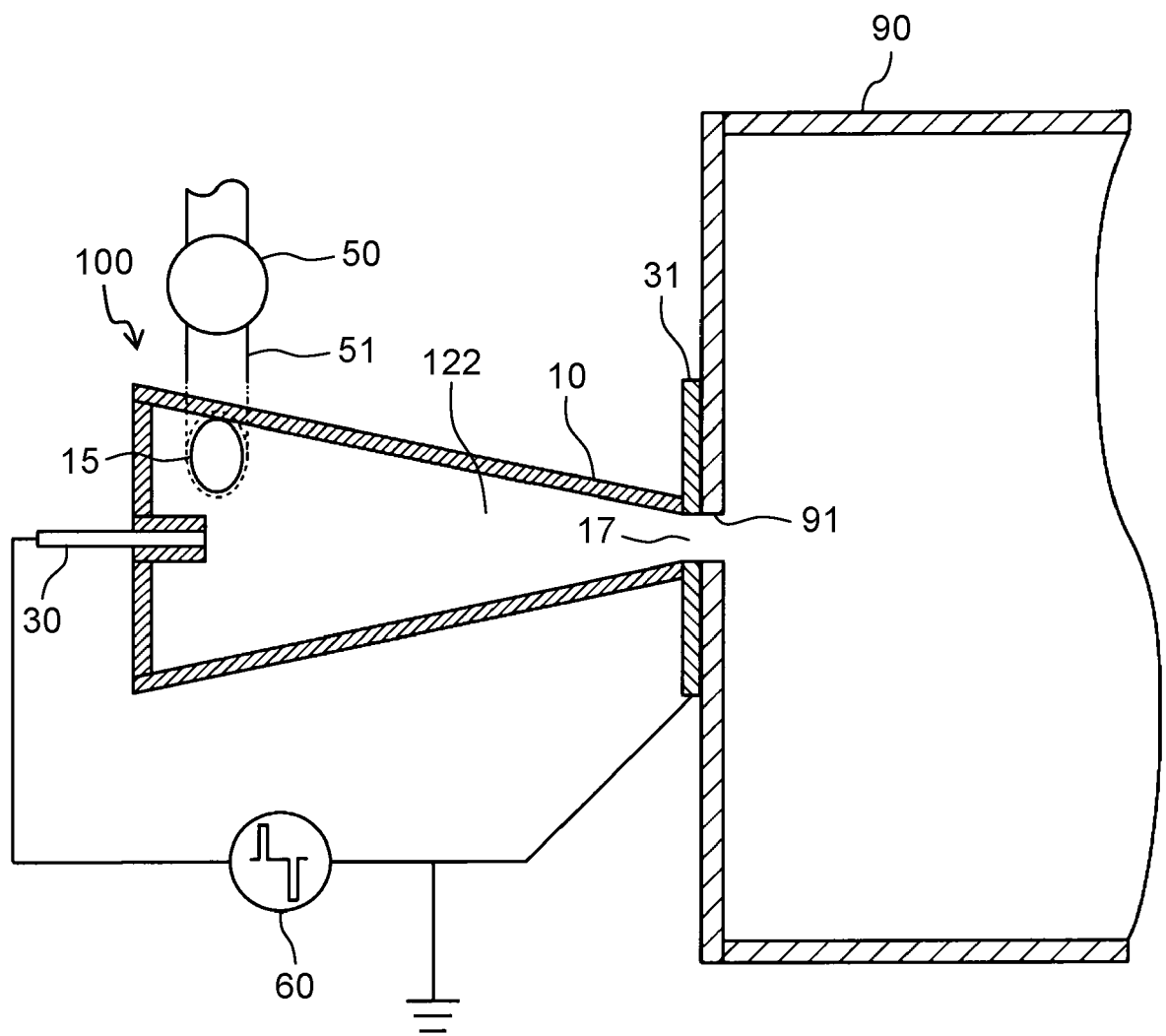
FIG. 8 is a side sectional view illustrating a modification example of the apparatus main body.
Figure 8:
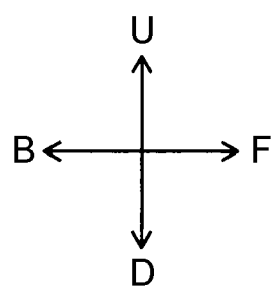

In Embodiment 1 to Embodiment 3, treatment tank 12 has a simple cylindrical shape, but can have various shapes as long as the treatment tank has a cylindrical shape of which sectional shape is circular and has a discharging portion of a hole shape narrowed on a central axis of the treatment tank or around the central axis at one end portion of the treatment tank. For example, as illustrated in FIG. 7, the same effect can be obtained even in treatment tank 121 in which circular tubes having different radii are combined. In FIG. 7, a configuration in which a radius on an introduction portion side is larger than a radius on a discharging portion side is provided. Alternatively, even in treatment tank 122 of a conical shape illustrated in FIG. 8, the same effect can be obtained. It is preferable that, in order to prevent rotating flow F1 from sliding in forward direction F, a conical shape in which an inner diameter of a cross section continuously decreases is provided as illustrated in FIG. 8.

Figure 9A:
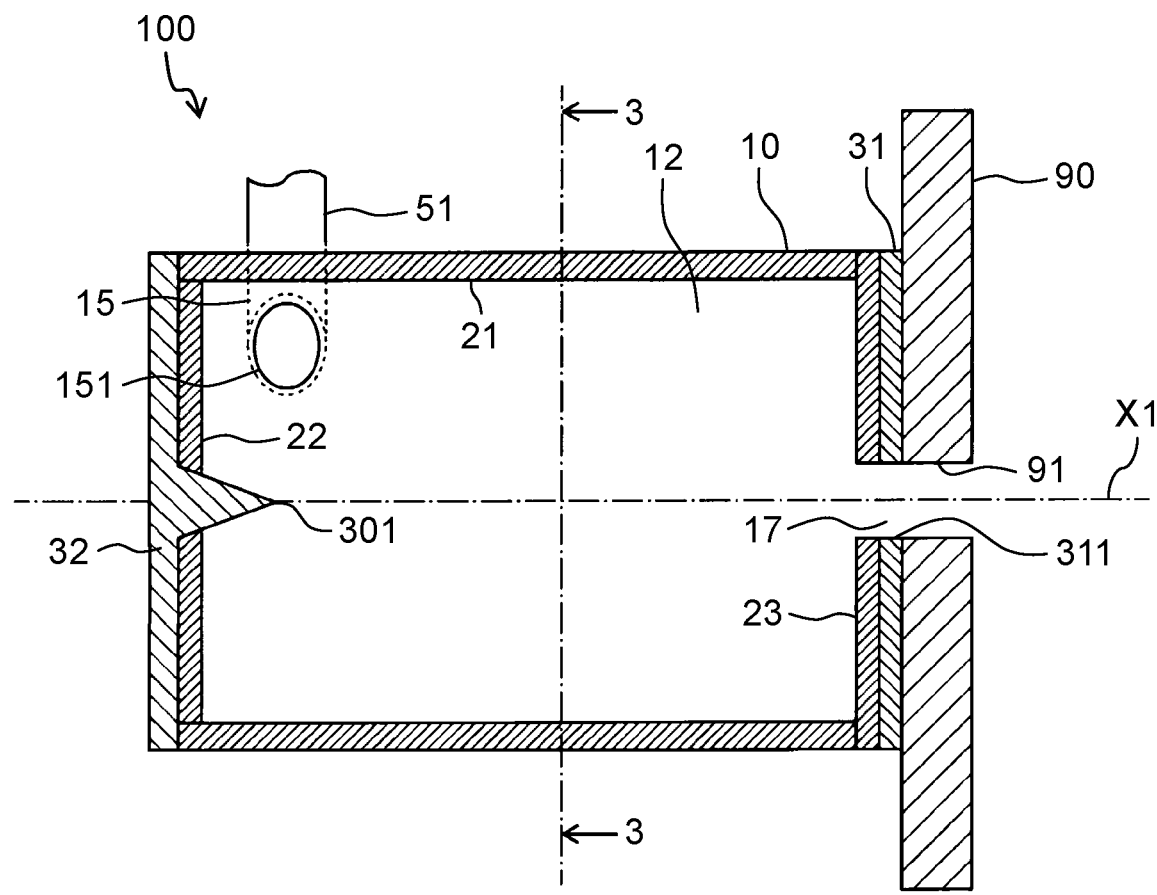
FIG. 9A is a side sectional view illustrating a modification example of the apparatus main body.
Figure 9A:
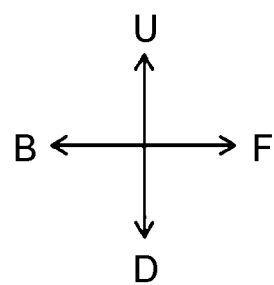
Figure 9B:
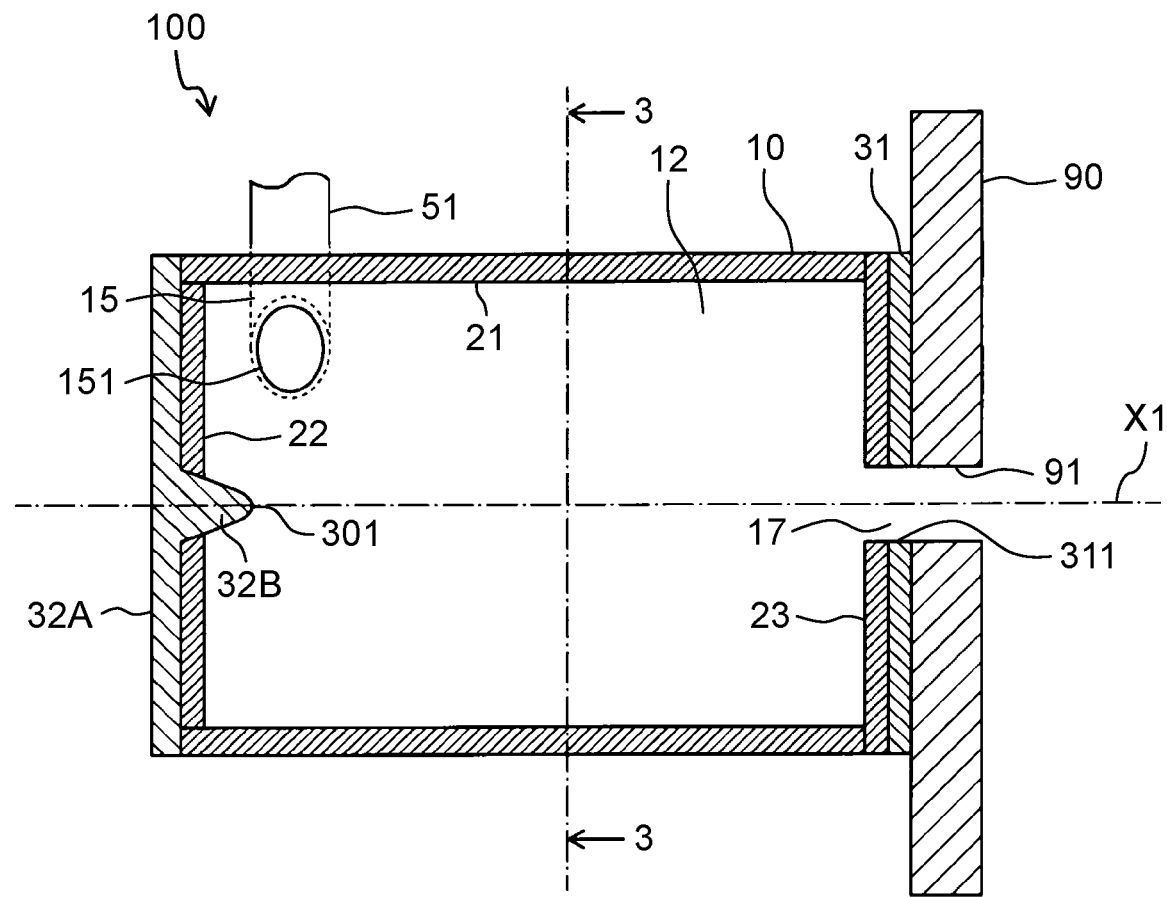
FIG. 9B is a side sectional view illustrating a modification example of the apparatus main body different from FIG. 9A.
Figure 9B:
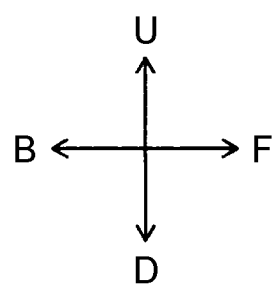

In addition, in Embodiment 1 to Embodiment 3, first electrode 30 has a shape of a bar electrode, but the shape is not limited to this as long as first electrode 30 has a shape in which electrolysis is concentrated on right end portion 301 of first electrode 30. For example, as illustrated in FIG. 9A, plate-shaped first electrode 32 having a pointed conical shape toward a discharging portion side may be used. In addition, as illustrated in FIG. 9B, plate-shaped first electrode 32A having a mountain-shaped projection portion 32B protruding so as to curve toward the discharging portion side in a central portion may be used instead of the conical shape. In first electrode 32A, since a central portion closest to plasma P to be generated easily wears out, an electrode having projection portion 32B of a mountain shape making a central portion protrude into treatment tank 12 is more preferable than a simple flat electrode because the electrode has a long life. More preferably, instead of first electrode 32 of a plate shape, a rod electrode may be used which facilitates transmission of an electrode into treatment tank 12 when the electrode wears out.

Figure 10:
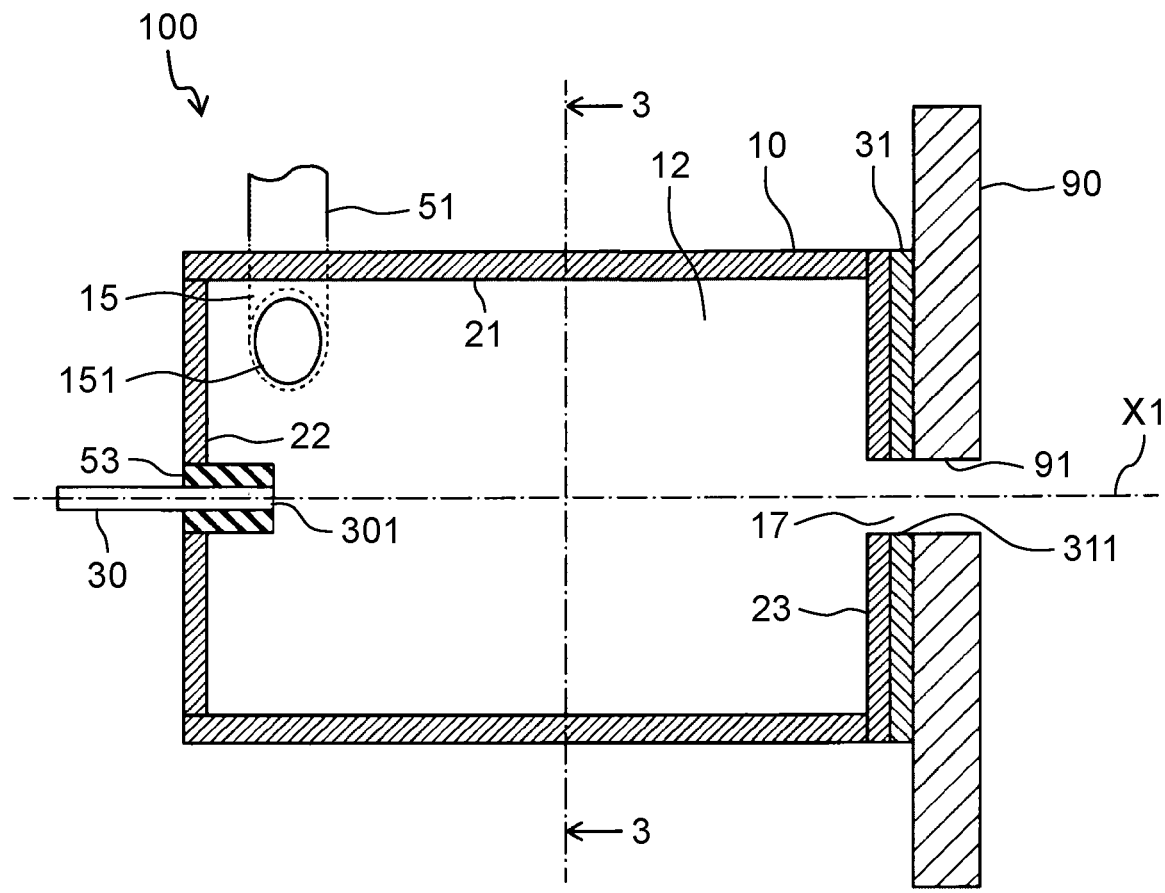
FIG. 10 is a side sectional view illustrating a modification example of the apparatus main body.
Figure 10:
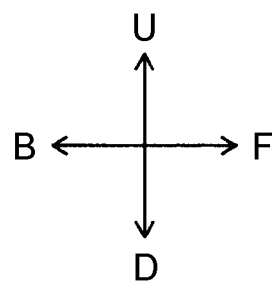

In addition, as illustrated in FIG. 10, the same effect can be obtained by adopting a structure in which first electrode 30 and insulator 53 are attached to second inner wall 22 without using electrode supporting tube 24 of first electrode 30. It is preferable that, in order to suppress electrolysis of water or generation of Joule heat, it is preferable that a portion except for right end portion 301 of first electrode 30 necessary for generating plasma and a connection portion between first electrode 30 and power source 60 is covered by an insulator.

In addition, in Embodiment 1 to Embodiment 3, a material of first electrode 30 is, for example, tungsten, but is not limited in particular as long as a material is conductive. It is preferable that a metal material capable of accomplishing a high bactericidal effect by causing a Fenton reaction is used if coming into contact with hydrogen peroxide in water. For example, a stainless steel (SUS), copper or copper tungsten may be used.

Figure 11:
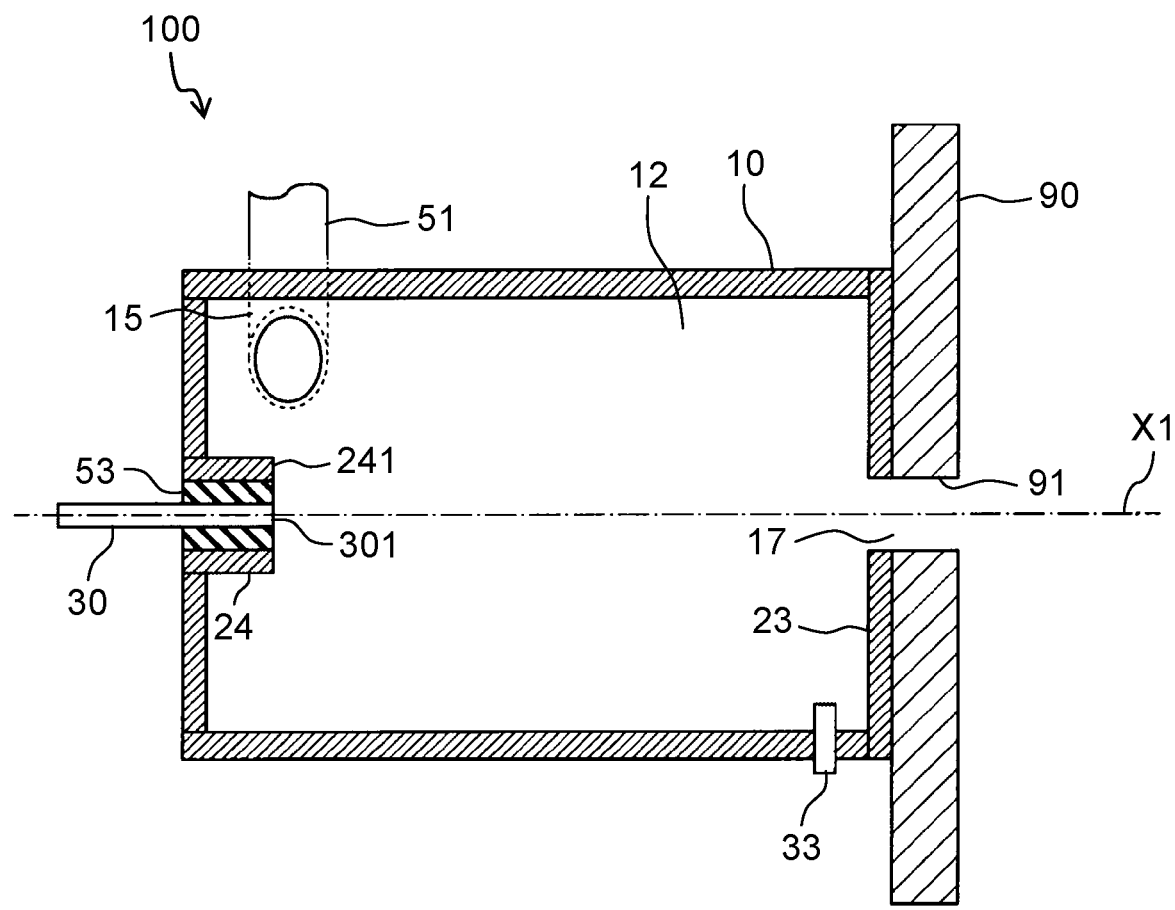
FIG. 11 is a side sectional view illustrating a modification example of the apparatus main body.
Figure 11:
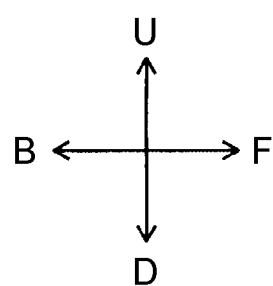
Figure 12:
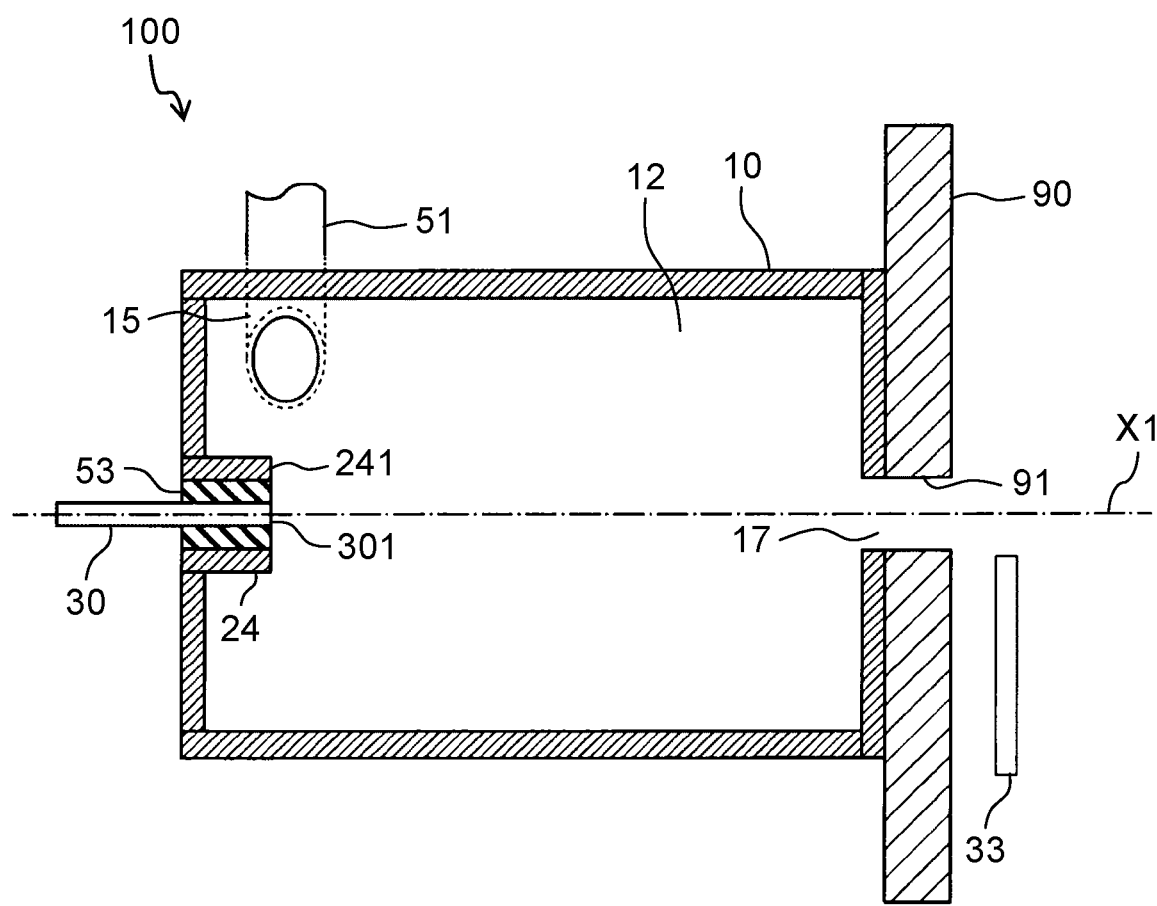
FIG. 12 is a side sectional view illustrating a modification example of the apparatus main body.
Figure 12:
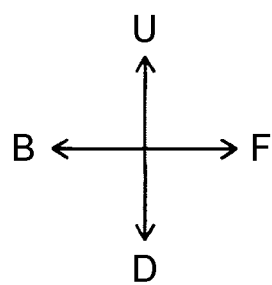
Figure 13:
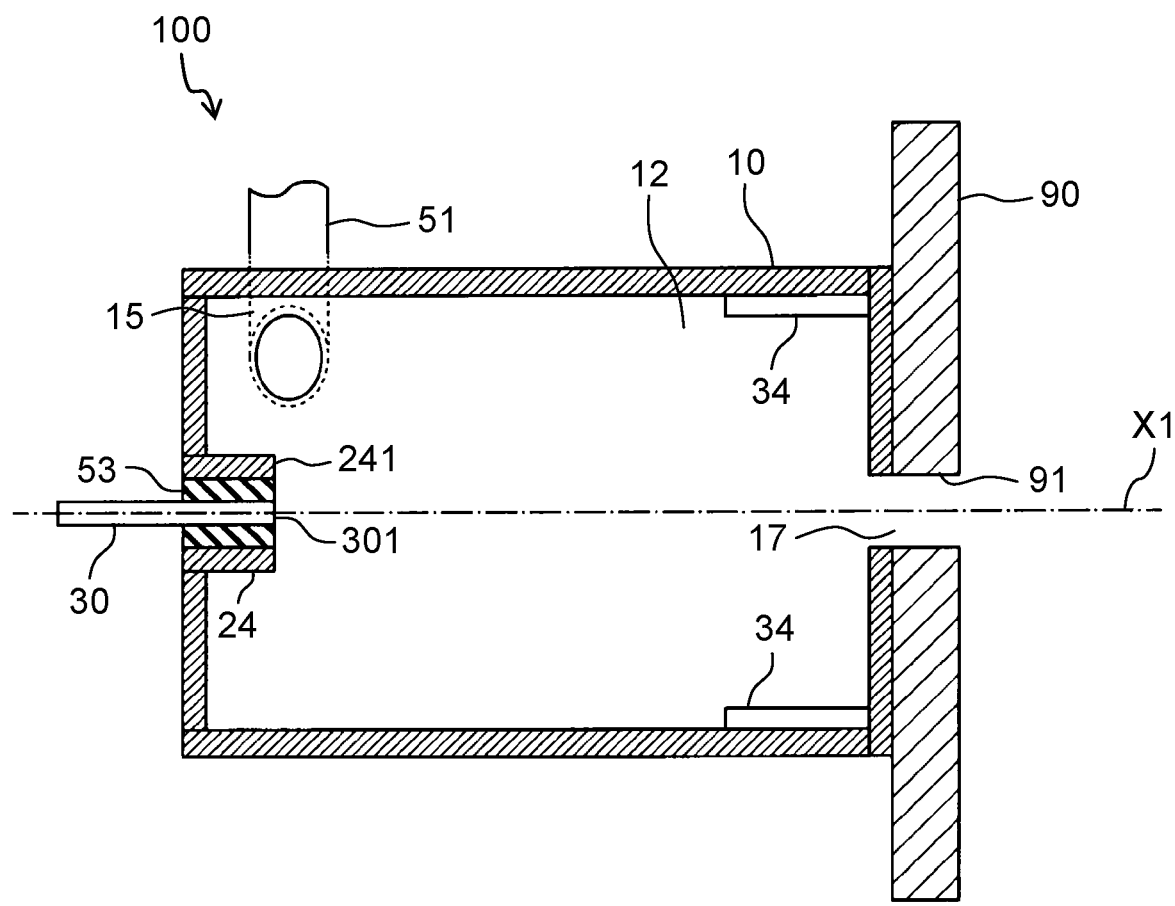
FIG. 13 is a side sectional view illustrating a modification example of the apparatus main body.
Figure 13:
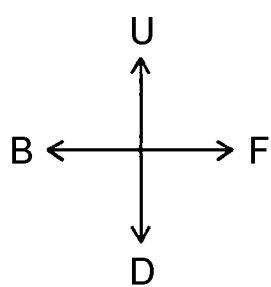

In Embodiment 1 to Embodiment 3, second electrode 31 is disposed in discharging portion 17, but is not limited as long as at least a part of the second electrode grounded in treatment tank 12 is disposed. For example, as for a disposition location, the same effect can be obtained even if second electrode 33 of a rod shape is disposed on a side of central axis X1 of first inner wall 21 as illustrated in FIG. 11. In addition, as illustrated in FIG. 12, second electrode 33 of a bar shape may be disposed in storage tank 90 outside treatment tank 12 and around modification liquid supplier 91 of the storage tank 90. In addition, as illustrated in FIG. 13, cylindrical second electrode 34 may be disposed in the inside of first inner wall 21. In addition, opening 311 has a circular shape, but may have a polygonal shape, and furthermore, the second electrode may be configured to combine a plurality of divided metal members. It is preferable that, in order not to disturb rotating flow F1, the second electrode has a plate shape having a round hole or a cylindrical shape. In addition, the shorter a distance between gas phase G and the second electrode is, the smaller the resistance of water is, and the Joule heat can be suppressed, and thereby, the second electrode may be disposed in discharging portion 17 where a space between gas phase G and the second electrode is short, or around discharging portion 17.

The amount of flow of circulation water L1 introduced into treatment tank 12 is set to the amount of flow at which gas phase G occurs in rotating flow F1 according to a shape of treatment tank 12 and the like. In addition, in a case where a pulse voltage applied to first electrode 30 and second electrode 31 is applied to monopolarity not bipolarity, or a voltage, a pulse width, a frequency, or the like can be appropriately set to a value capable of generating plasma P in gas phase G generated in rotating flow F1.

Furthermore, as long as the effect of the present disclosure can be obtained, power source 60 may be a high-frequency power source or the like other than a pulse power source. It is preferable that, since pH between the electrodes is biased by electrolysis of water, bipolar application which can alternately exchange a cathode and an anode is used.

Figure 14A:
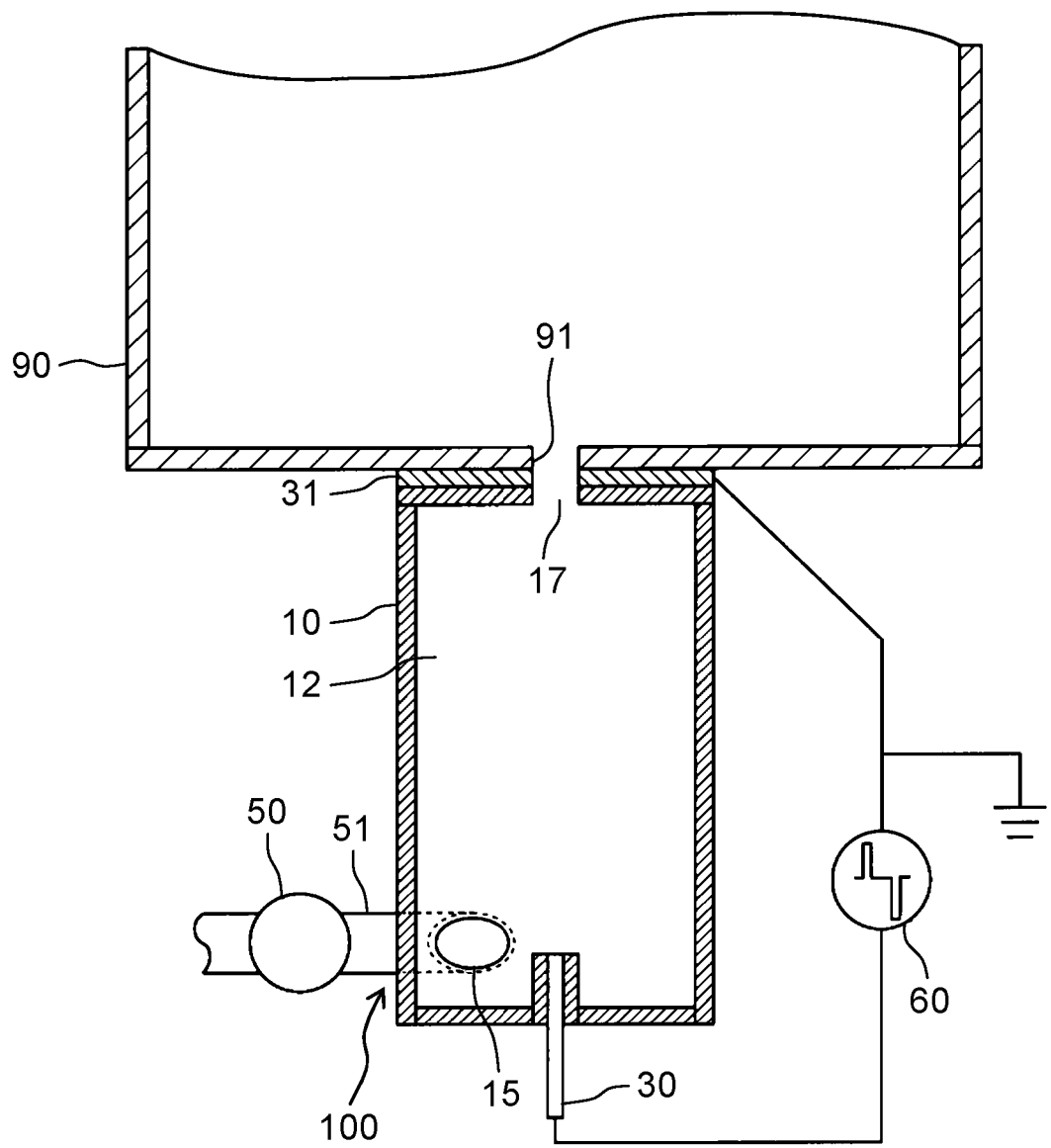
FIG. 14A is a side sectional view illustrating a modification example of the apparatus main body.
Figure 14A:
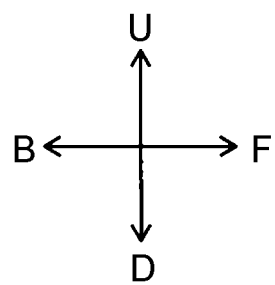

Storage tank 90 is a tank, but is not limited to this as long as storage tank 90 has a shape in which water is retained, in order to shear rotating flow F1. For example, a pipe for transporting modification liquid may be used. It is preferable that, in order to fill discharging portion 17 with circulation water L1 to prevent air from entering into treatment tank 12, apparatus main body 10 discharges the modification liquid upward and storage tank 90 is placed on an upper side of apparatus main body 10 as illustrated in FIG. 14A.

Figure 14B:
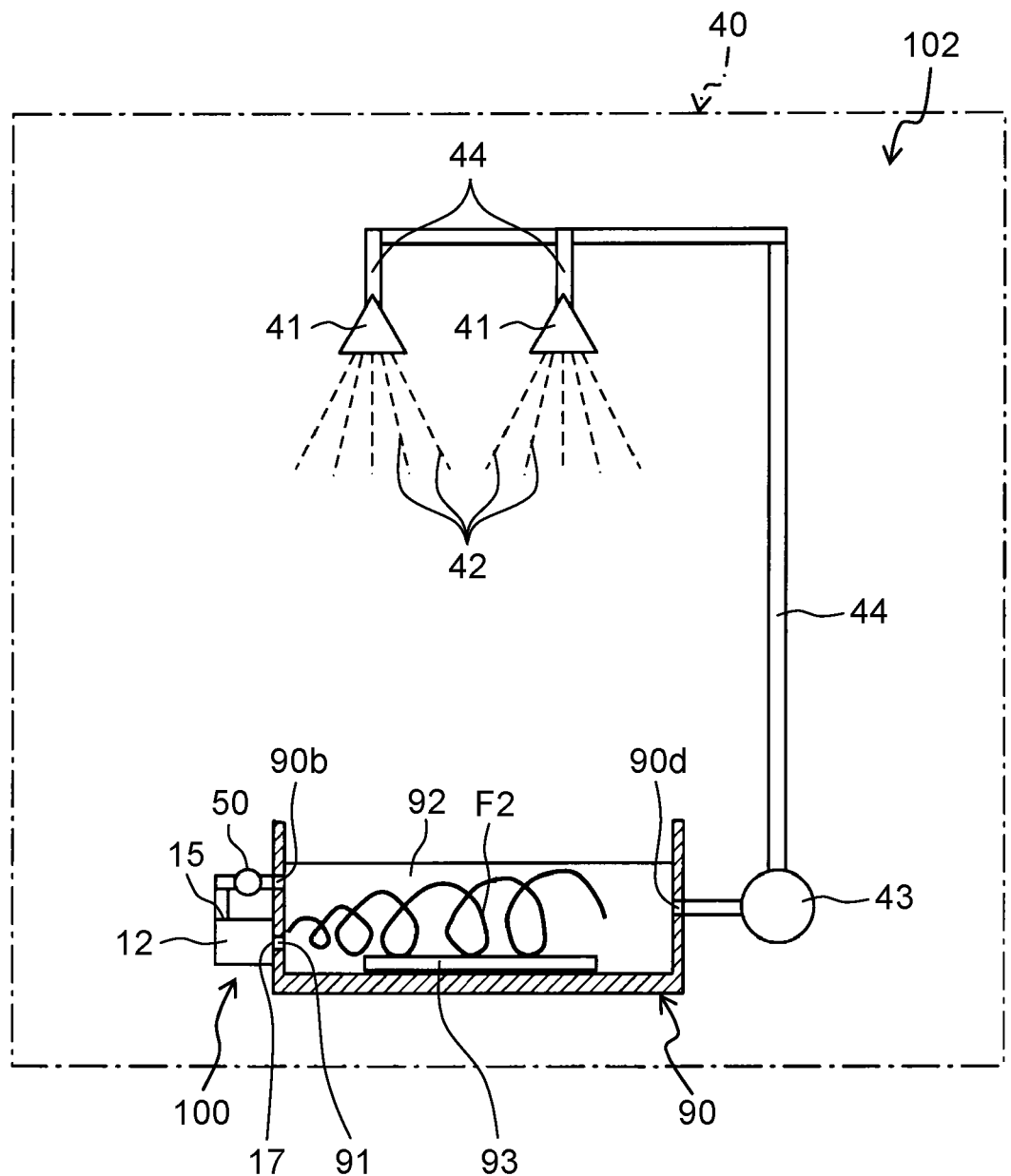
FIG. 14B is a side sectional view of a modification example of the apparatus main body in which a copper material is disposed in a part of one storage tank.
Figure 15:
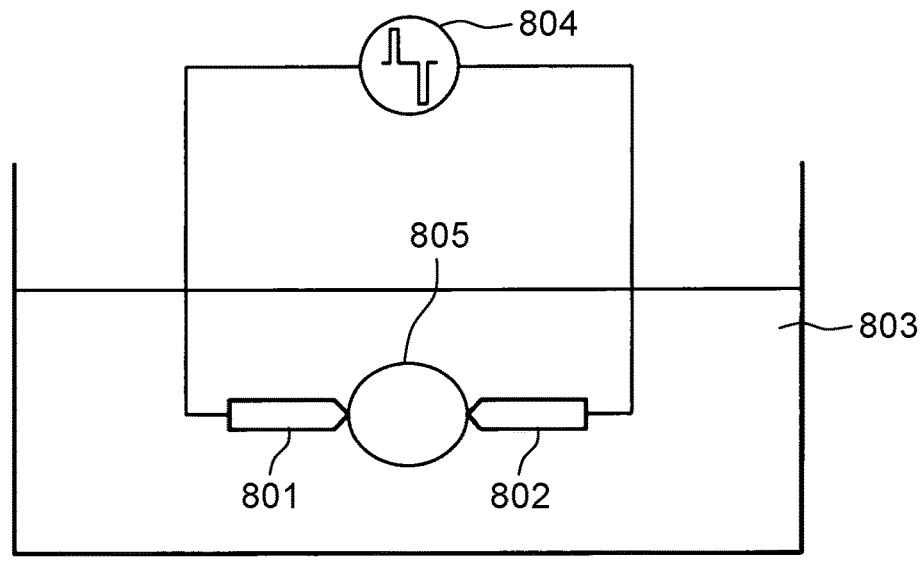
FIG. 15 is a schematic configuration diagram of a modification liquid generating apparatus of related art.
Figure 16:
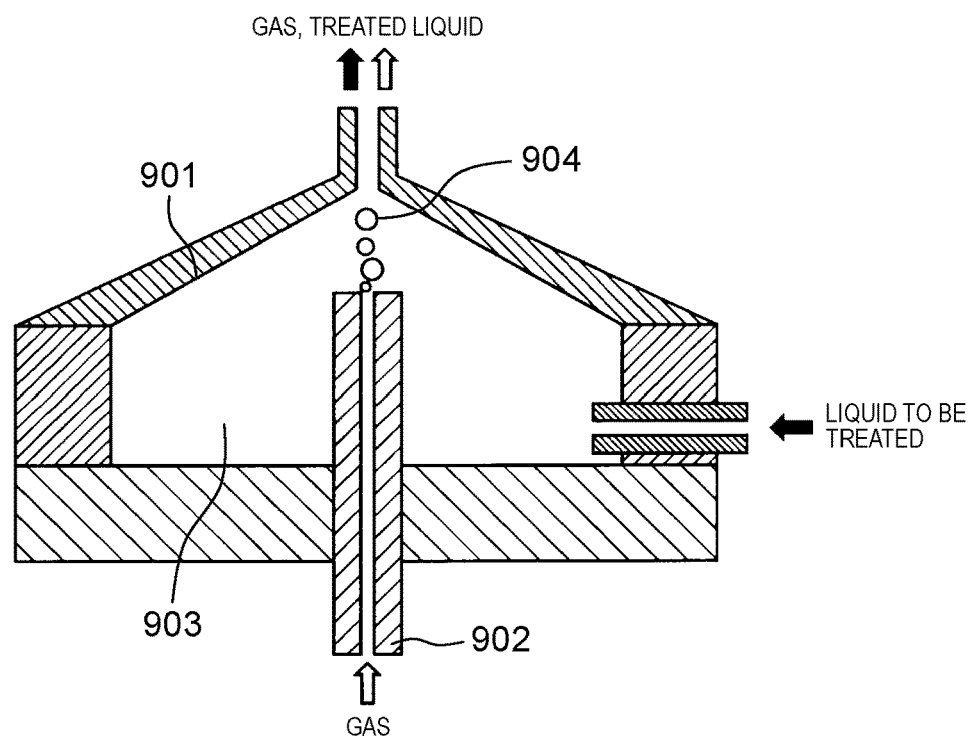
FIG. 16 is a schematic configuration diagram of a modification liquid generating apparatus of related art including a gas introducing apparatus.

In addition, water may not permeate a material configuring storage tank 90. In addition, for example, plate member 93 containing copper or iron capable of accomplishing a high bactericidal effect by causing a Fenton reaction with hydrogen peroxide water which is one of modification components, can be used for a part or the whole of storage tank 90 as illustrated in FIG. 14B. In addition, plate member 93 may be disposed in storage tank 90 as a member other than storage tank 90. In short, if plate member 93 comes into contact with the modification liquid in storage tank 90, the plate member causes a Fenton reaction with hydrogen peroxide water which is one of the modification components, thereby, accomplishing a high bactericidal effect.

In Embodiment 1 to Embodiment 3, circulation water L1 is modified, but liquid to be modified is not limited to water. For example, ethanol may be used.

As described above, Embodiment 1 to Embodiment 3 according to the present disclosure are described, Embodiments 1 to Embodiment 3 described above are merely examples for implementing the present disclosure. Thus, the present disclosure is not limited to Embodiment 1 to Embodiment 3 described above, and Embodiment 1 to Embodiment 3 described above can be appropriately modified to be implemented without departing from the spirit of the present disclosure.

That is, by appropriately combining any embodiments or modification examples among the embodiments or the various modification examples, it is possible to accomplish each of the effects. In addition, it is possible to perform a combination of the embodiments, a combination of the examples, or a combination of the embodiments and the examples, and it is also possible to perform a combination of features in different embodiments or examples.

Summarization

A space modification apparatus according to one embodiment of the present disclosure includes treatment tank 12, first electrode 30, second electrode 31, power source 60, storage tank 90, liquid supplier 50, nozzle 41, and supply pump 45. Treatment tank 12 generates a gas phase around a rotating center of a rotating flow of a liquid by rotating the liquid which is introduced from introduction portion 15 around a central axis X1 to generate the rotating flow, and includes discharging portion 17 generating the rotating flow by rotating the liquid which is introduced from introduction portion 15 between introduction portion 15 and the discharging portion, and thereafter, discharges the liquid as a modification liquid. At least a part of first electrode 30 is disposed in treatment tank 12 so as to be in contact with the liquid in treatment tank 12. Second electrode 31 is disposed so as to be in contact with the liquid in treatment tank 12. Power source 60 generates modification components in the modification liquid by applying a voltage between first electrode 30 and second electrode 31 to generate plasma in the gas phase. Storage tank 90 stores the modification liquid which is discharged from discharging portion 17 of treatment tank 12. Liquid supplier 50 reintroduces stored water which is discharged into and retained in storage tank 90 as the modification liquid from introduction portion 15 of treatment tank 12 in treatment tank 12, and allows the stored water to circulate between treatment tank 12 and storage tank 90. Nozzle 41 is connected to stored water discharging portion 90b of storage tank 90 and discharges the stored water in the storage tank into treatment target space 40 in a form of mist. Supply pump 45 supplies the stored water from storage tank 90 to nozzle 41. Accordingly, space modification apparatus sprays or scatters the stored water from nozzle 41.

Storage tank 90 may be disposed below nozzle 41 and an upper portion of the storage tank is open, and the stored water that is sprayed or scattered from nozzle 41 may be collected in storage tank 90 and the liquid that is collected in storage tank 90 may come into contact with the modification liquid in storage tank 90.

First electrode 30 may be disposed so as to be in contact with or to be positioned around the gas phase that is generated around the rotating center of the rotating flow of the liquid.

Treatment tank 12 may have cylindrical or truncated conical first inner wall 21 that generates the rotating flow by rotating the liquid which is supplied from introduction portion 15, and first electrode 30 may be disposed on central axis X1 of first inner wall 21 or around central axis X1.

First electrode 30 may be disposed on one end portion side on central axis X1 or around central axis X1, second electrode 31 may be disposed on the other end portion side on central axis X1 or around central axis X1, introduction portion 15 may be disposed on the one end portion side of central axis X1, and discharging portion 17 may be disposed on the other end portion side of central axis X1.

Second electrode 31 may be a plate-shaped electrode that is disposed so as to surround at least a part of a periphery of central axis X1 of first inner wall 21 on the other end portion side of first inner wall 21.

Second electrode 31 may be disposed on a side of central axis X1 of first inner wall 21 on the other end portion side of first inner wall 21.

Second electrode 31 may be a cylindrical electrode that is disposed so as to surround at least a part of central axis X1 of first inner wall 21 on the other end portion side of first inner wall 21.

A space modification apparatus according to another embodiment of the present disclosure includes treatment tank 12, first electrode 30, second electrode 31, power source 60, storage tank 90, liquid supplier 50, nozzle 41, and supply pump 45. Treatment tank 12 generates a gas phase around a rotating center of a rotating flow of a liquid by rotating the liquid which is introduced from introduction portion 15 around central axis X1 to generate the rotating flow, and includes discharging portion 17 generating the rotating flow by rotating the liquid which is introduced from introduction portion 15 between introduction portion 15 and the discharging portion, and thereafter, discharges the liquid as a modification liquid. At least a part of first electrode 30 is disposed in treatment tank 12 so as to be in contact with the liquid in treatment tank 12. Second electrode 31 is disposed so as to be in contact with the liquid in treatment tank 12. Power source 60 generates modification components in the modification liquid by applying a voltage between first electrode 30 and second electrode 31 to generate plasma in the gas phase. Storage tank 90 stores the modification liquid which is discharged from discharging portion 17 of treatment tank 12. Liquid supplier 50 reintroduces stored water which is discharged into and retained in storage tank 90 as the modification liquid from introduction portion 15 of treatment tank 12 in treatment tank 12, and allows the stored water to circulate between treatment tank 12 and storage tank 90. Nozzle 41 is disposed above storage tank 90 in treatment target space 40 and discharges a liquid toward an upper opening of storage tank 90 in a form of mist. Supply pump 45 supplies the liquid to nozzle 41. Accordingly, after the liquid that is supplied from supply pump 45 to nozzle 41 is sprayed or scattered from nozzle 41 and is collected in the upper opening of storage tank 90, the liquid comes into contact with the modification liquid in storage tank 90.

A space modification apparatus according to the above-described aspect of the present disclosure generates a modification liquid containing modification components (radical derived from a liquid, a compound or the like) from a liquid by generating plasma in the liquid, and can spray or scatter the generated modification liquid in the form of mist to a space to be treated. Therefore, the space modification apparatus according to the above-described aspect of the present disclosure can be used for sterilization, deodorization, various environmental improvement, or the like, and can be used for, for example, a scrubber, a spray type sterilization system for a food factory or the like.

What is claimed is:

1. A space modification apparatus comprising:
   a treatment tank configured to generate a gas phase around a rotating center of a rotating flow of a liquid by rotating the liquid which is introduced from an introduction portion around a central axis of the treatment tank to generate the rotating flow, the treatment tank including a discharging portion which is configured to discharge the liquid as a modification liquid after generation of the rotating flow by rotating the liquid which is introduced from the introduction portion between the introduction portion and the discharging portion, the treatment tank not including a gas introduction path;
   a first electrode of which at least a part is in the treatment tank and is configured to be in contact with the liquid in the treatment tank;
   a second electrode configured to be in contact with the liquid in the treatment tank;
   a power source configured to apply a voltage between the first electrode and the second electrode to generate plasma in the gas phase to generate modification components in the modification liquid;
   a storage tank configured to store the modification liquid which is discharged from the discharging portion;
   a liquid supplier configured to reintroduce stored water which is discharged into and retained in the storage tank as the modification liquid from the introduction portion in the treatment tank, and allow the stored water to circulate between the treatment tank and the storage tank;
   a nozzle that is connected to a stored water discharging portion of the storage tank and is configured to discharge the stored water in the storage tank into a treatment target space in a form of mist; and
   a supply pump configured to supply the stored water from the storage tank to the nozzle,
   wherein the nozzle is configured to spray or scatter the stored water therefrom.

2. The space modification apparatus of claim 1,
   wherein the storage tank is below the nozzle and an upper portion of the storage tank is open, and
   wherein the storage tank is configured to collect the stored water that is sprayed or scattered from the nozzle such that the liquid that is collected in the storage tank comes into contact with the modification liquid in the storage tank.

3. The space modification apparatus of claim 1, wherein the first electrode is configured to be in contact with or around the gas phase that is generated around the rotating center of the rotating flow of the liquid.

4. The space modification apparatus of claim 1, wherein the treatment tank has a cylindrical or truncated conical first inner wall configured to cause the rotating flow of the liquid by rotating the liquid which is introduced from the introduction portion, and wherein the first electrode has a rod shape or a conical shape, and a central axis of the first electrode coincides with a central axis of the cylindrical or truncated conical first inner wall.

5. The space modification apparatus of claim 4, wherein the first electrode is on a first end portion side on the central axis of the treatment tank or around the central axis of the treatment tank, wherein the second electrode is on a second end portion side on the central axis of the treatment tank or around the central axis of the treatment tank, wherein the introduction portion is on the first end portion side of the central axis of the treatment tank, and wherein the discharging portion is on the second end portion side of the central axis of the treatment tank.

6. The space modification apparatus of claim 5, wherein the second electrode is a plate-shaped electrode that surrounds at least a part of a periphery of the central axis of the cylindrical or truncated conical first inner wall on the second end portion side of the cylindrical or truncated conical first inner wall.

7. The space modification apparatus of claim 5, wherein the second electrode is on a side of the central axis of the cylindrical or truncated conical first inner wall on the second end portion side of the cylindrical or truncated conical first inner wall.

8. The space modification apparatus of claim 5, wherein the second electrode is a cylindrical electrode that surrounds at least a part of the central axis of the cylindrical or truncated conical first inner wall on the second end portion side of the cylindrical or truncated conical first inner wall.

9. A space modification apparatus comprising:

a treatment tank configured to generate a gas phase around a rotating center of a rotating flow of a liquid by rotating the liquid which is introduced from an introduction portion around a central axis of the treatment tank to generate the rotating flow, the treatment tank including a discharging portion which is configured to discharge the liquid as a modification liquid after generation of the rotating flow by rotating the liquid which is introduced from the introduction portion between the introduction portion and the discharging portion, the treatment tank not including a gas introduction path;

a first electrode of which at least a part is in the treatment tank and is configured to be in contact with the liquid in the treatment tank;

a second electrode configured to be in contact with the liquid in the treatment tank;

a power source configured to apply a voltage between the first electrode and the second electrode to generate plasma in the gas phase to generate modification components in the modification liquid;

a storage tank configured to store the modification liquid which is discharged from the discharging portion;

a liquid supplier configured to reintroduce stored water which is discharged into and retained in the storage tank as the modification liquid from the introduction portion in the treatment tank, and allow the stored water to circulate between the treatment tank and the storage tank;

a nozzle that is above the storage tank in a treatment target space and is configured to discharge a liquid toward an upper opening of the storage tank in a form of mist; and a supply pump configured to supply the liquid to the nozzle, wherein the upper opening of the storage tank is configured to collect the liquid that is sprayed or scattered from the nozzle such that the liquid comes into contact with the modification liquid in the storage tank.

* * * * *